(12) United States Patent
DeLuca et al.

(10) Patent No.: US 6,916,834 B2
(45) Date of Patent: Jul. 12, 2005

(54) PREPARATIONS AND USE OF AN AH RECEPTOR LIGAND, 2-(1'H-INDOLE-3'-CARBONYL)-THIAZOLE-4-CARBOXYLIC ACID METHYL ESTER

(75) Inventors: Hector F. DeLuca, Deerfield, WI (US); Jiasheng Song, Madison, WI (US); Margaret Clagett-Dame, Deerfield, WI (US); Richard E. Peterson, Oregon, WI (US); William M. Westler, Madison, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 34 days.

(21) Appl. No.: 10/074,102

(22) Filed: Feb. 12, 2002

(65) Prior Publication Data

US 2002/0183524 A1 Dec. 5, 2002

Related U.S. Application Data

(60) Provisional application No. 60/268,809, filed on Feb. 14, 2001.

(51) Int. Cl.$^7$ ................. A61K 31/427; C07D 277/20
(52) U.S. Cl. ................................ 514/365; 548/201
(58) Field of Search .................... 548/201, 181; 514/365

(56) References Cited

U.S. PATENT DOCUMENTS

| 3,285,931 A | | 11/1966 | Huisgen | |
| 5,336,685 A | * | 8/1994 | Prochaska et al. | 514/455 |
| 6,323,228 B1 | * | 11/2001 | BaMaung et al. | 514/365 |

OTHER PUBLICATIONS

Song et al, Proceedings of the National Acadamey of Sciences 99 (23) 14694 2002.*

L. Chunchatprasert, et al., A New Synthetic Route to Pyrrolo[3,2–b]carbazoles, 1H–Benzofuro[3,2–f]indoles and 1H–[1]Benzothieno[2,3–f]indoles, J. Chem. Soc. Perkin Trans. pp. 1779–1783, 1992.

L. Chunchatprasert and P.V.R. Shannon, "Further Observations on and Novel Products from Acid–catalyzed Indole–Pyrrole Condensations: Fomation of Pyrrole[2,3–b]carbazoles," J. Chem. Soc. Perkin Trans. pp. 1765–1772, 1994.

P. Dharmasena, et al., "Antitumour Heterocycles. Part 12. The Synthesis of New Hydroxypyrrolocarbazoles and Hydroxypyridocarbazoles," J. Chem. Research pp. 12–13, 1996.

O. Hankinson, "The Aryl Hydrocarbon Receptor Complex," Annu. Rev. Pharmacol. Toxicol. 35:307–340, 1995.

P.H. jellinck, et al., "Ah Receptor Binding Properties of Indole Carbinols and Induction of Hepatic Estradiol Hydroxylation," Biochemical Pharmacology 45(5):1129–1136, 1993.

A.J. Phillips, et al., "Synthesis of Functionalized Oxazolines and Oxazoles with DAST and Deoxo–Fluor," Organic Letters 2(8):1165–1168, 2000.

L. Poellinger, Regulation fo Intracellular Dioxin (Aryl Hydrocarbon) Receptor Function by Dietary Indole Derivatives, Hormonally Active Agents in Food Symposium, pp. 121–127, 1998.

Adachi, J. et al. "Indirubin and indigo are potent aryl hydrocarbon receptor ligand present in human urine", J. Biol. Chem. 276(34):31475–31478 (2001).

Chen, I., Safe, S., and Bjeldanes, L. "Indole–3–carbinol and diindolylmethane as aryl hydrocarbon (Ah) receptor agonists and antagonists in T47D human breast cancer cells", Biochem. Pharmacol. 51(8):1069–1076 (1996).

Chen, Y. H..et al. "Regulation of CYP1A1 by indolo[3,2–b]carbazole in murine hepatoma cells", J. Biol. Chem. 270(38):22548–22555 (1995).

Cheung, Y. L., Snelling, J., Mohammed, N. N. D., Gray, T. J. B., and Ioannides, C. "Interaction with the aromatic hydrocarbon receptor, cyp 1a induction, and mutagenicity of a series of diaminotoluenes—implications for their carcinogenicity", Toxicol. Appl. Pharmacol. 139(1):203–211 (1996).

Garrison, P.M. et al. "Species–specific recombinant cell lines as bioassay systems for the detection of 2,3,7,8–tetrachlorodibenzo–p–dioxin–like chemicals," Fund. Appl. Toxicol. 30:194–203 (1996).

Heathpagliuso, S. et al. "Activation of the Ah receptor by tryptophan and tryptophan metabolites", Biochem. 37(33):11508–11515 (1998).

Lee, I. J. et al. "Transcriptional induction of the cytochrome p4501a1 gene by a thiazolium compound, yh439", Mol. Pharmacol. 49(6):980–988 (1996).

Liu, R. M.et al. "Regulation of [Ah] gene battery enzymes and glutathione levels by 5,10–dihydroindeno[1,2–b]indole in mouse hepatoma cell lines", Carcinogenesis. 15(10):2347–2352. (1994).

Poellinger, L. "Mechanistic aspects–the dioxin (aryl hydrocarbon) receptor". Food Add. Contam. 17(4):261–266 (2000).

Poland, A. and Glover, E. "Chlorinated dibenzo–p–dioxin: Potent inducers of __–aminolevulinic acid synthetase and aryl hydrocarbon hydroxylase. II. A study of the structure–activity relationship", Mol. Pharmacol. 9:736–747 (1973).

Rannung, A. et al. "Certain photooxidized derivatives of tryptophan bind with very high affinity to the Ah receptor and are likely to be endogenous signal substances," J. Biol. Chem. 262:15422–15427 (1987).

(Continued)

Primary Examiner—Golam M M Shameem
(74) Attorney, Agent, or Firm—Quarles & Brady LLP

(57) ABSTRACT

Preparation, use, and structure of endogenous Ah receptor ligand is disclosed.

7 Claims, 7 Drawing Sheets

OTHER PUBLICATIONS

Schaldach, C. M., Riby, J., and Bjeldanes, L.F.. "Lipoxin A(4): A new class of ligand for the Ah receptor", Biochem. 38(23):7594–7600 (1999).

Sinal, C. J. and Bend, J. R. "Aryl hydrocarbon receptor–dependent induction of cyp 1a1 by bilirubin in mouse hepatoma hepa 1c1c7 cells", Mol. Pharmacol. 52(4):590–599 (1997).

Stephensen, P. U. et al. "N–methoxyindole–3–carbinol is a more efficient inducer of cytochrome P–450 1A1 in cultured cells than indol–3–carbinol", Nutr Cancer Internatl. J. 36(1):112–121 (2000).

Vasiliou, V., Shertzer, H. G., Liu, R. M., Sainsbury, M., and Nebert, D. W. "Response of [Ah] battery genes to compounds that protect against menadione toxicity", Biochem. Pharmacol. 50(11):1885–1891 (1995).

Washburn, B. S. et al. "Brevetoxin–6 (pbtx–6), a nonaromatic marine neurotoxin, is a ligand of the aryl hydrocarbon receptor". Arc. Biochem. Biophy. 343(2):149–156 (1997).

Whitlock, J.P., Jr., "Genetic and molecular aspects of 2,3,7,8–tetrachlorodibenzo–p–dioxin action," Ann. Rev. Pharmacol. Toxicol. 30:251–277 (1990).

A. J. Philips, et al., "Synthesis of Functionalized Oxazolines and Oxazoles with DAST and Deoxo–Fluor," Organic Letter 2(8):1165–1168, 2000.

R. Susilo, et al., "Formation of Thiazolidine–4–Carboxylic Acid Represents a Main Metabolic Pathway of 5–Hydroxytryptamine in Rat Brain," J. Neurochemistry 52(6):1793–1800, 1989.

* cited by examiner

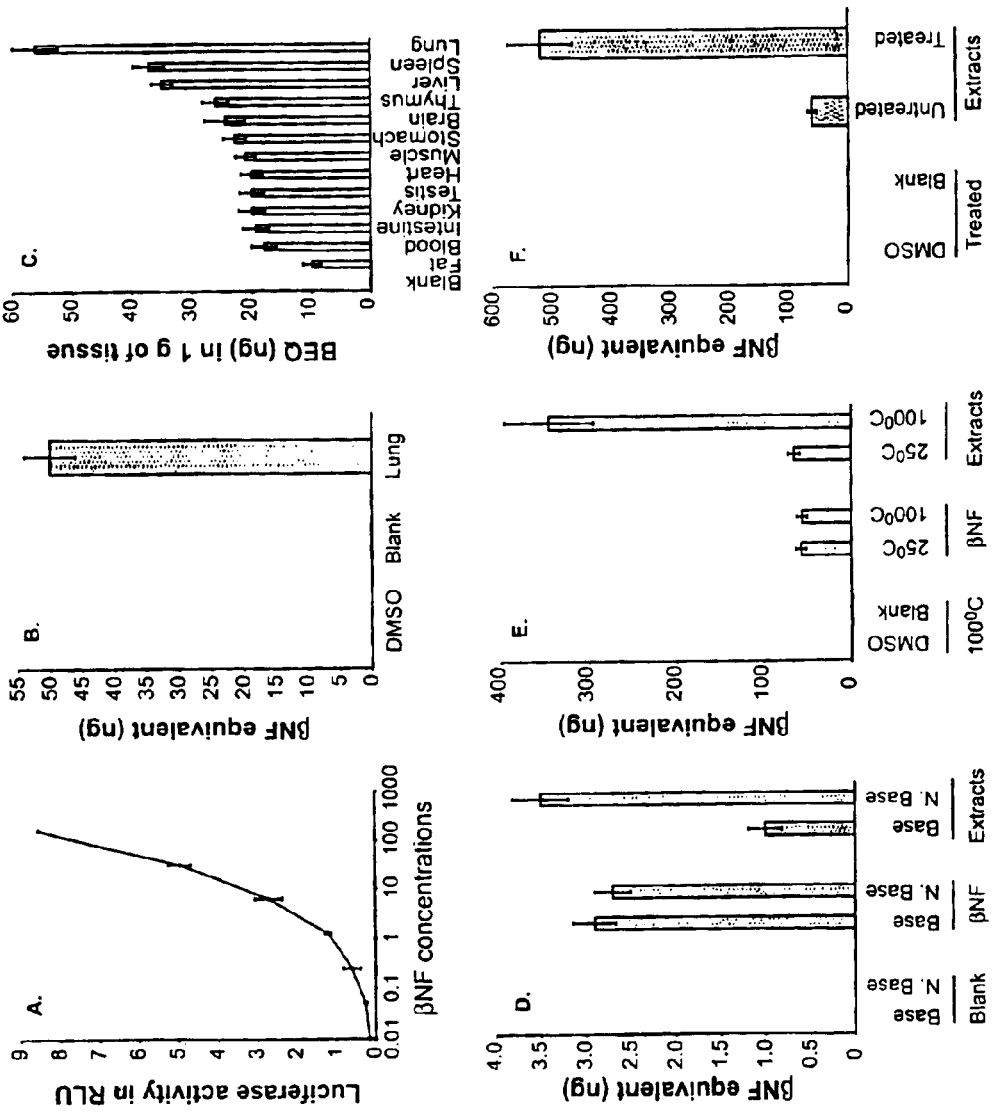
Fig. 1. Reporting Cell Response to βNF and Tissue Extracts

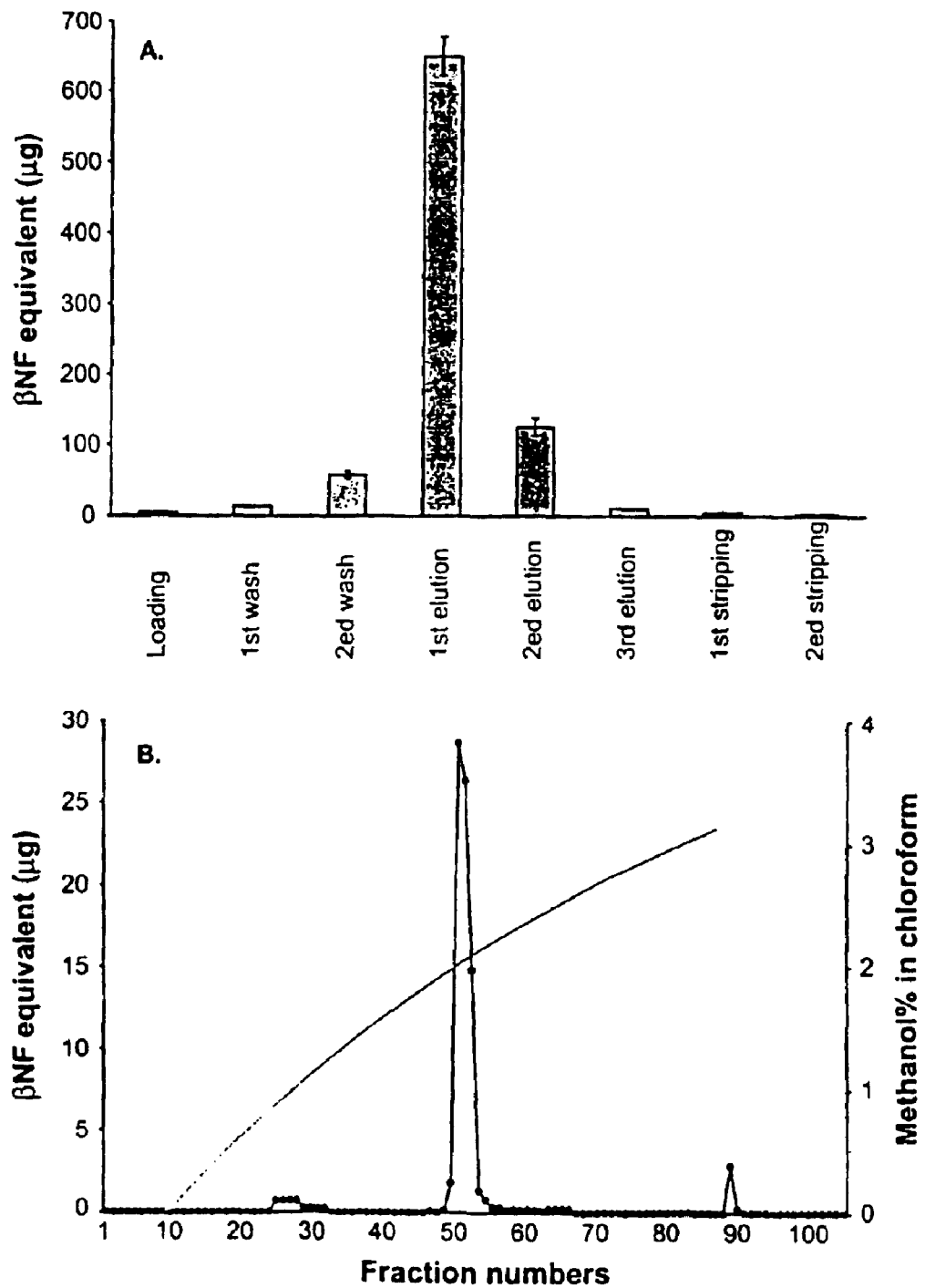
Fig. 2. Preliminary Purification of AhR Ligands

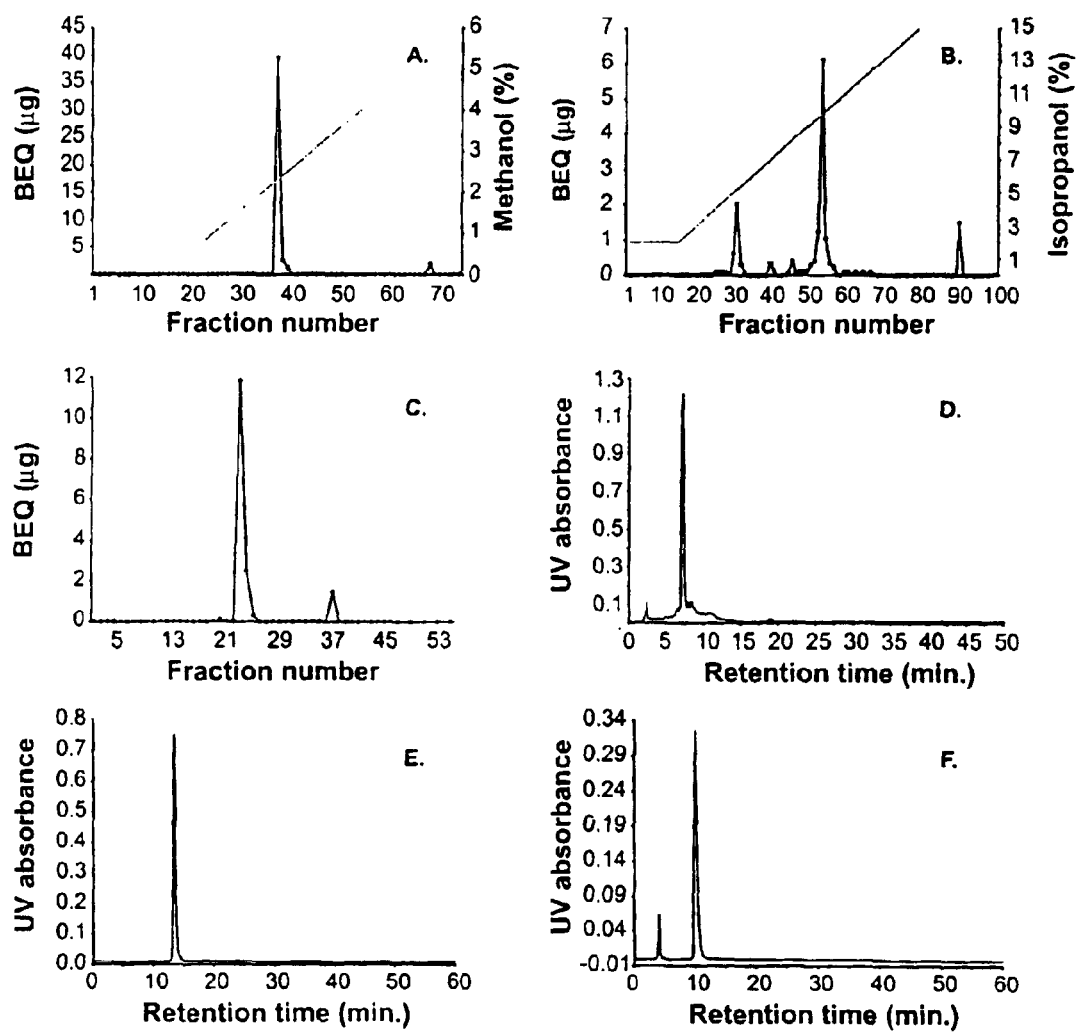
Fig. 3. HPLC Purification of AhR Ligands

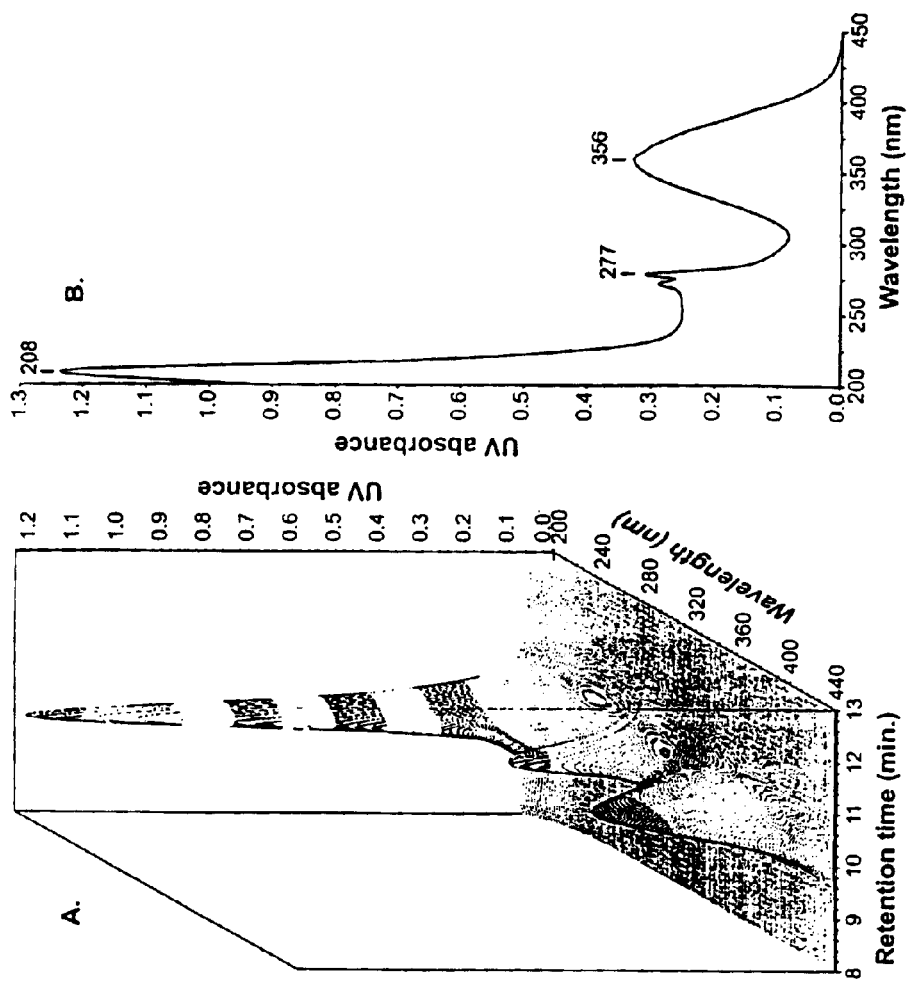
Fig. 4. HPLC Chromatogram and UV Spectrum of the Purified AhR Ligand

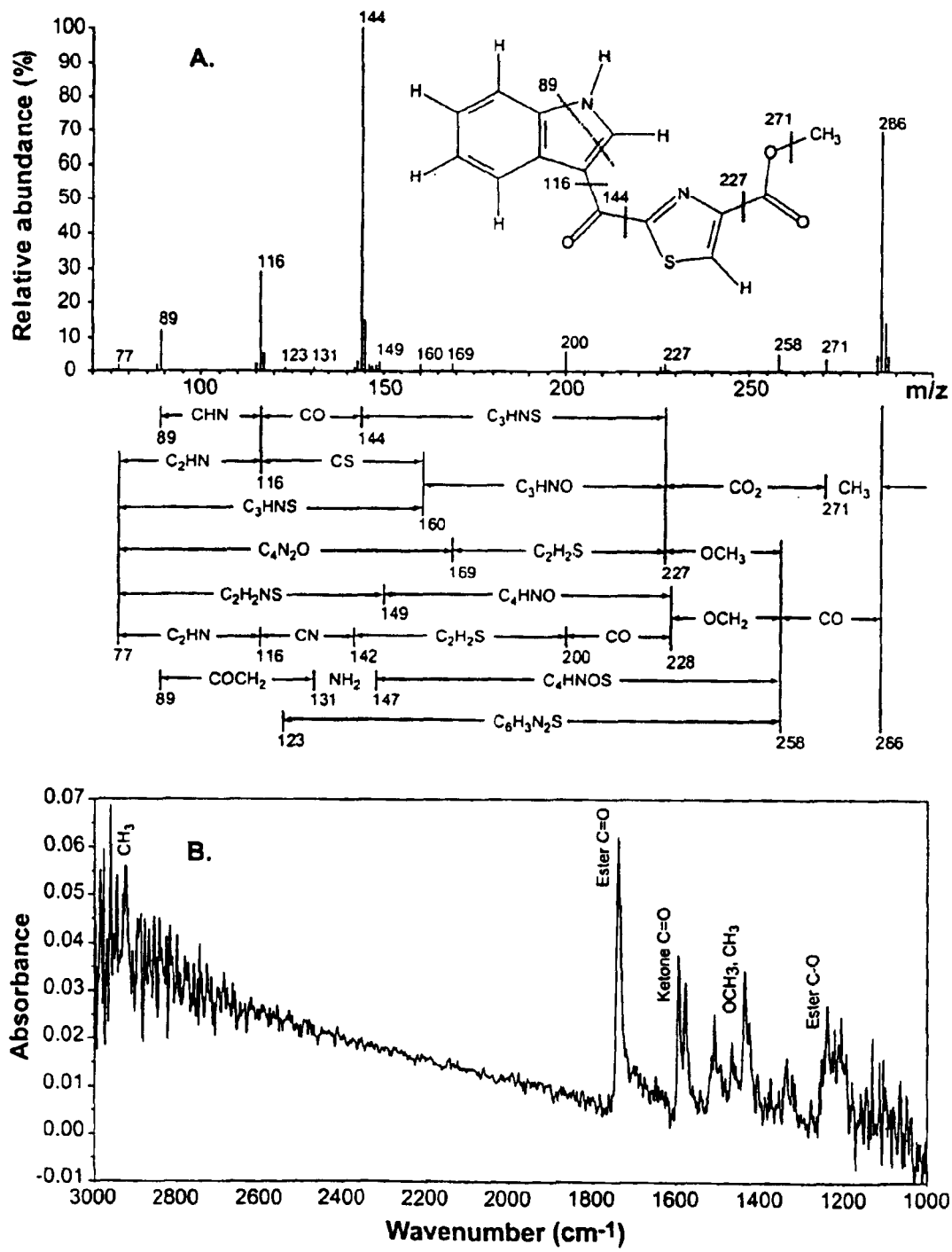
Fig. 5. Electron Impact Mass and FT-IR Spectra

Fig. 6. Proton NMR Spectrum and Proton-carbon-13 Correlation
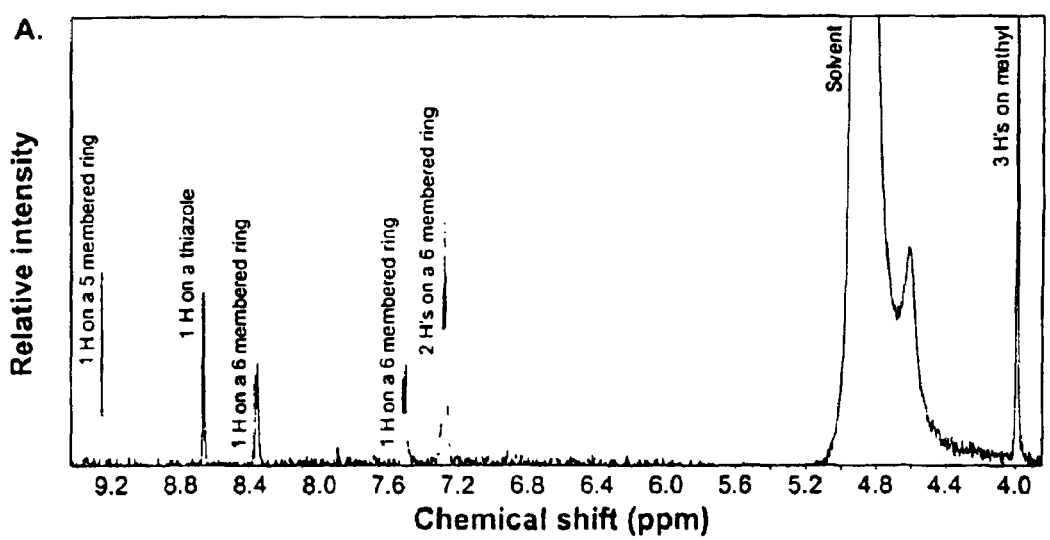
| ¹H (ppm) | Number of ¹H | HSQC ¹³C (ppm) | HMBC ¹³C (ppm) | ¹³C (ppm) | ¹³C (ppm) |
|---|---|---|---|---|---|
| 3.99 | 3 | 54.50 | 165.00 | | |
| 7.27 | 1 | 125.10 | | | |
| 7.28 | 1 | 126.15 | | | |
| 7.50 | 1 | 114.45 | 125.10 | 129.50 | |
| 8.36 | 1 | 124.25 | 126.15 | 139.50 | |
| 8.67 | 1 | 135.25 | 150.10 | 173.10 | |
| 9.25 | 1 | 141.05 | 115.10 | 129.50 | 139.50 |

Fig. 7. The Structure of ITE and Dose Responses of ITE and βNF
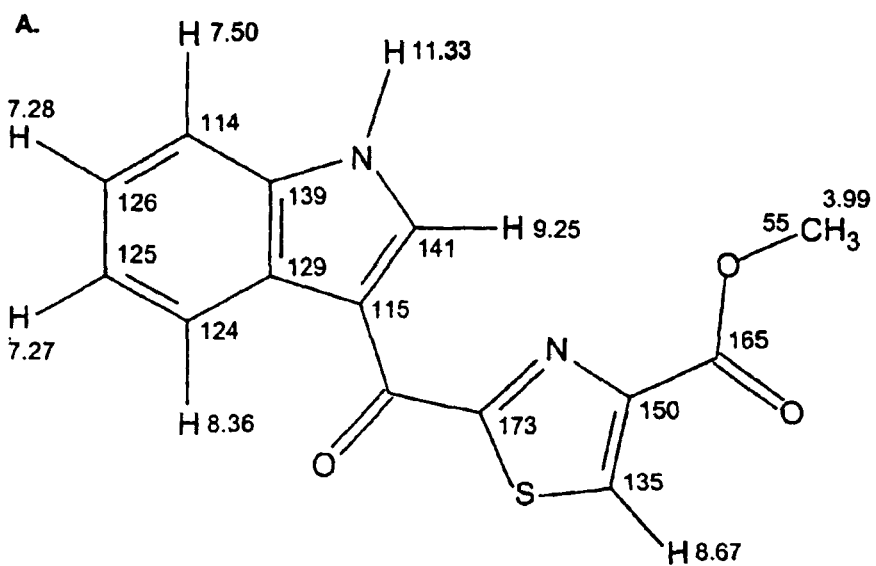
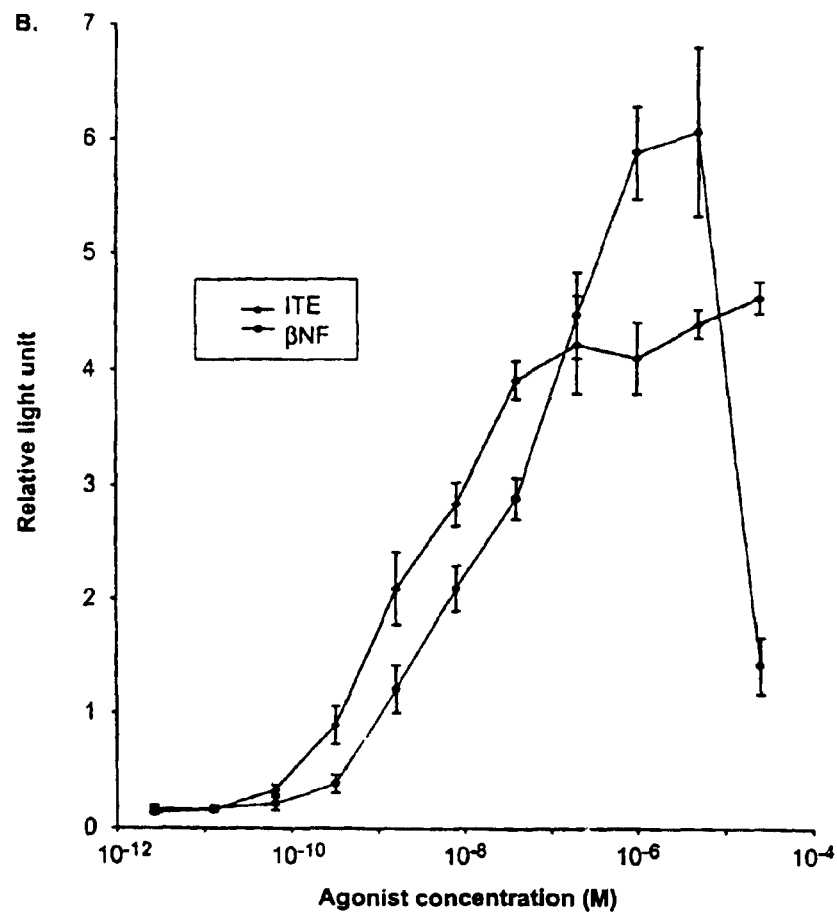

PREPARATIONS AND USE OF AN AH RECEPTOR LIGAND, 2-(1'H-INDOLE-3'-CARBONYL)-THIAZOLE-4-CARBOXYLIC ACID METHYL ESTER

CROSS-REFERENCE TO RELATED APPLICATION

This application claims priority to provisional patent application Ser. No. 60/268,809, filed Feb. 14, 2001, incorporated by reference herein.

STATEMENT REGARDING FEDERALLY SPONSORED RESEARCH OR DEVELOPMENT

--

BACKGROUND OF THE INVENTION

The Aryl Hydrocarbon Receptor. The aryl hydrocarbon receptor (AhR) is a ligand inducible transcription factor mediating a broad spectrum of biological processes upon binding to its ligand. Besides induction of enzymes in the cytochrome P450 family, the receptor appears involved with cell proliferation, tumor promotion, immune suppression, vitamin A depletion, and developmental and reproductive abnormalities (Fletcher, et al., 2001; Safe, 2001; Gu, et al., 2000; Poellinger, 2000; Schmidt and Bradfield, 1996; Whitlock, et al., 1997). The liganded receptor also causes cell cycle arrest, apoptosis, adipose differentiation, and anti-estrogen effects (Bonnesen, et al., 2001; Elferink, et al., 2001; Shimba, et al., 2001, 1998; Safe, 2001; McDougal et al., 2001, 2000; Elizondo, et al., 2000; Puga, et al., 2000; Alexander, et al., 1998). The presence of the receptor was proposed and evidenced in 1970's (Poland, et al., 1976). The coding sequence for the receptor was cloned in 1990's and revealed that the AhR is a member of an emerging basic Helix-Loop-Helix/Pas-Arnt-Sim (bHLH/PAS) transcription factor super family (Burbach, et al., 1992).

The bHLH/PAS Super Family of Transcription Factors. The bHLH/PAS super family includes Drosophila Per, Arnt (Ah receptor nuclear translocator, the dimerization partner of AhR and others), SIM1, SIM2, TRH, ARNT-2, the hypoxia inducible factor-1 (HIF-1α), SRC-1, TIF2, RAC3, MOPs 2–5 (Gu, et al., 2000; Hogenesch, et al., 1997; Wilk, et al., 1996), and endothelial PAS domain protein (EPAS-1) (Tian, et al., 1997). These bHLH proteins contain the 300 amino acid PAS domain, composed of two 50 amino acid degenerate direct repeats (Burbach, et al., 1992; Dolwick, et al., 1993). The basic region is important for DNA binding, and the HLH and PAS domains are involved in dimerization, and for AhR, in ligand binding (Swanson and Bradfield, 1993). The transactivation domains of the AhR and ARNT map to their carboxyl termini (Jain, et al., 1994). Members of this super family are master developmental regulators and it is intriguing to speculate similar roles for AhR and ARNT. Besides with AhR, ARNT forms heterodimers also with HIF-1α, PER, SIM, MOP2 (Hogenesch, et al., 1997), and EPAS-1 (Tian, et al., 1997) and an ARNT-related protein is postulated to heterodimerize with TRH (Wilk, et al., 1996). This promiscuity of ARNT indicates AhR-independent roles for ARNT and suggests the possibility of cross talk between AhR and the other bHLH/PAS signaling pathways.

The Homeostatic Response to Hypoxia: Role of HIF-1a/ARNT-Mediated Gene Expression. Vertebrates require molecular oxygen for vital metabolic processes. Homeostatic responses elicited by hypoxia include erythropoiesis, angiogenesis, and glycolysis. These adaptive responses serve to increase oxygen delivery or activate alternative metabolic pathways that do not require oxygen in hypoxic tissues. In response to hypoxia, HIF-1α translocate into the nucleus where they form heterodimers with ARNT (Gradin, et al., 1996; Schmidt and Bradfield. 1996). The HIF-1α/ARNT heterodimers bind to hypoxia response elements increasing transcription of genes involved in maintaining oxygenation of tissues. The hypoxia-inducible gene products include erythropoietin (EPO), vascular endothelial growth factor (VEGF), and glycolytic enzymes (Maltepe and Simon, 1998).

The Mode of Action of AhR/ARNT Signaling Pathway. The cytoplasmic form of AhR is associated with 2 molecules of heat shock protein (hsp90) and some other cellular factors (Poellinge,. 2000; Whitlock, 1990). After ligand binding, the hsp90 and the other factors dissociate and AhR is activated. The activated AhR then translocates into the nucleus and dimerizes with its partner ARNT (Probst, et al., 1993). AhR/ARNT heterodimers recognize and bind the so-called xenobiotic response elements (XREs) found in promoters of AhR controlled genes to alter gene expression (Whitlock, 1990). Another potential mechanism involves competition between AhR and either HIF-1α and/or EPAS-1 for dimerization with ARNT. Since AhR, HIF-1α and EPAS-1 require dimerization with ARNT to control the expressions of their target genes, activation of AhR might reduce the availability of free ARNT to such an extent that it becomes rate limiting for other signaling pathways. Decreased availability of ARNT could lead to decreased expression of vital hypoxia-regulated genes and angiogenesis blockage, for example, by inhibiting HIF-1α signaling (Gradin, et al., 1996; Schmidt and Bradfield, 1996).

The Known AhR Ligands. Among the first discovered human-made ligands for the AhR are the chemicals known as polycyclic aromatic hydrocarbons such as 3-methylcholanthrene and benzo[α]pyrene. A much more potent and higher affinity ligand, 2,3,7,8-tetrachlorodibenzo-p-dioxin (TCDD), was discovered (Poland and Glover, 1973). Another structural group of compounds, halogenated aromatic hydrocarbons, was recognized as the receptor ligands. The compounds with different structural characteristics from the groups mentioned were also found to have binding affinity to AhR. This group is represented by bilirubin (Phelan, et al., 1998; Sinal and Bend, 1997), lipoxin A(4) (Schaldach, et al., 1999), brevetoxin-6 (Washburn, et al., 1997), diaminotoluene (Cheung, et al., 1996), and YH439, a thiazolium compound (Lee, et al., 1996). Among most of the human-made AhR ligands, TCDD is one of the most potent agents for AhR and is the prototype compound used to study the mechanism of AhR action and dioxin toxicity. The term "dioxins" has been used to refer to any of the PCDDs (polychlorinated dibenzo-p-dioxins), PCDFs (polychlorinated dibenzofurans), or PCBs (polychlorinated biphenyls) that cause the same biological responses, by the same mechanism as TCDD.

The AhR Ligands with an Indole Moiety. The other recognized AhR ligands with an indole moiety are of special interest. This group consists of tryptamine, indole acetic acid (Heathpagliuso, et al., 1998), indole-3-carbinol and its derivatives (Stephensen, et al., 2000; Chen, et al., 1996; Vasiliou, et al., 1995; Liu, et al., 1994; Jellinck et al. 1993), and indolo[3,2-b]carbazole (ICZ) (Chen et al. 1995; Kleman et al. 1994). Closely related to ICZ, 6-formylindolo[3,2-b]carbazole derived from tryptophan by UV oxidation has higher affinity than that of TCDD to the receptor (Rannug, et al., 1995, 1987). Some of the indole derived AhR ligands displayed their interesting properties: binding to the receptor, low toxicity, antiestrogenic and antitumorigenic. Actually, clinical studies have been launched for indole-3-carbinol as an anticarcinogenic and antitumorigenic remedy for patients with high risk of tumorigenesis (Preobrazhenskaya and Korolev, 2000).

Identity of the Endogenous AhR Ligand and Physiological Functions of the Ah Receptor System Are not Resolved. Okamoto, et al. (1993) observed that exposure of adult male rats to hyperoxia (95% oxygen) caused induction of CYP1A1 in the lung and CYP1A1 and 1A2 in the liver. The induction of CYP1A1/1A2 is usually associated with the binding of AhR to its ligands. One hypothesis to explain CYP1A1/1A2 induction by hyperoxia is that an endogenous ligand(s) of the AhR is produced by hyperoxia, which activates the transcription of CYP1A1/1A2 genes (Okamoto, et al., 1993). Recently two human urinary products were isolated that bind to the AhR (Adachi, et al., 2001). Whether those products are endogenous ligands or not is undetermined because the identified compounds are indigo, a commonly used fabric dye, and indirubin, an isomer of indigo. Since they were isolated from urine, the question of whether they are urinary excretion products remains unanswered. Similarly, the bilirubin-related compounds (Phelan, et al., 1998; Sinal and Bend, 1997) and lipoxin A(4) (Schaldach, et al., 1999) are certainly endogenous in nature but whether they are the true ligands for the AhR has not yet been resolved. The response and affinity for the AhR appear to be, in fact, quite low for these compounds.

The generation of AhR-deficient mice illustrates possible physiological functions of the receptor in liver, heart, ovary, and the immune system, even though it is not conclusive at this point (Benedict, et al., 2000; Poellinger, 2000; Mimura, et al., 1997; Schmidt, et al., 1996; Fernandez-Salguero, et al., 1995). The significance of those findings is that they demonstrate a need for a functioning AhR signaling pathway in animal physiology. It is probable that endogenous AhR ligands in animal tissues are involved in carrying out this AhR signaling function.

Importance of Identifying the Endogenous AhR Ligands. Studies with human-made AhR ligands on this receptor system greatly advanced our understanding in this system. It is clear, however, that the AhR did not develop in an evolutionary sense to react to manufactured chemical agents. It is reasonable to suspect that there must be an endogenous ligand for the AhR, which should be nontoxic at tissue concentrations normally encountered in the body, rapidly cleared by metabolism, and utilized to activate the AhR only transiently in a regulatory capacity. Also, evidence shows that the different outcomes of the ligand-receptor mediated signaling processes are possible and dependent upon the nature of the ligands. A decisive factor dictating the consequences in the ligand-receptor mediated signal transducing systems is the final three dimensional conformation of the liganded receptor assumes because that conformation determines the ways the liganded receptor interacts with numerous other factors to transduce signals. Given the amino acid sequence of the receptor, the final three-dimensional structure of the liganded receptor is solely dependent on the structure of the ligand, which ultimately dictates the biological outcomes of the signaling system. To completely understand the physiological functions of the Ah receptor system and the potential therapeutic benefits this system may offer, the identification of the endogenous AhR ligand is an absolute necessity.

BRIEF SUMMARY OF THE INVENTION

We disclose herein the extraction, purification, identification, and applications of a novel endogenous Ah receptor ligand, 2-(1'H-indole-3'-carbonyl)-thiazole-4-carboxylic acid methyl ester.

In one embodiment, the present invention is a preparation of the endogenous Ah receptor ligand, either isolated from animal tissues or synthetically created. Preferably, the preparation is stable to boiling for 24 hours, soluble in 80% methanol: 20% water, stable overnight in two normal acid, and unstable in base. The preparation is preferably at least 60% pure, more preferably 90% pure, and most preferably 95% pure and characterized by its ultraviolet, infrared, mass, and nuclear magnetic resonance spectra as disclosed in Examples.

In a preferred embodiment of the present invention, the structure of the ligand is the structure displayed below and disclosed in FIG. 7A.

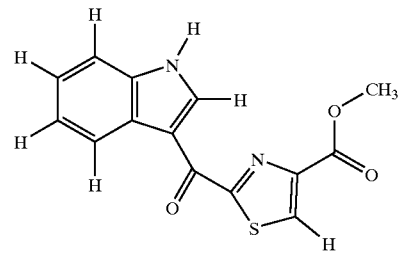

The present invention is also a method of reducing body weight of an animal, modulating the immune system of an animal, inhibiting the action of estrogens in an animal, decreasing testosterone production in an animal, treating pulmonary disorder or controlling angiogenesis or invasive cancer all comprising the step of treating an animal with an effective amount of the endogenous Ah receptor ligand preparation or an analog thereof.

In a preferred embodiment, the analog structure is as follows:

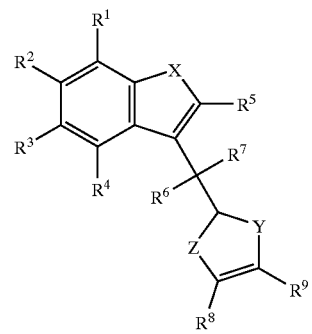

Where $R^1$, $R^2$, $R^3$, $R^4$, $R^5$, and $R^8$=H, lower alkyl (1–5 carbons), Br, F, Cl, O-acyl (1–5 C, or $OR^{10}$ where $R^{10}$=H, lower alkyl (1–5 C);

$R^6$ and $R^7$ taken together are =O; or when $R^6$=H, then $R^7$ can be H, OH, Br, F, Cl, $OR^{11}$ where $R^{11}$=alkyl (1–5 C); and when $R^7$=H, then $R^6$ can be H, OH, Br, F, Cl, $OR^{11}$ where $R^{11}$=alkyl (1–5 C);

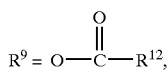

where $R^{12}$=H, alkyl (1–5 C), aryl, fluoromethyl, difluoromethyl, or trifluoromethyl; or $R^9$ can be

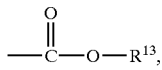

where $R^{13}$=H, alkyl (1–5 C), aryl, fluoromethyl, difluoromethyl, or trifluoromethyl;

$R^9$ can be

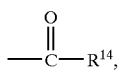

where $R^{14}$=H, alkyl (1–5 C), fluoromethyl, difluoromethyl, or trifluoromethyl; or $R^9$ can also be

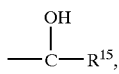

where $R^{15}$=H, alkyl (1–5 C), fluoromethyl, difluoromethyl, or trifluoromethyl, and X, Y, Z can be any of C, N, O, or S.

It is an object of the present invention to provide a preparation of the endogenous Ah receptor ligand derived from animal tissues.

It is another object of the present invention to provide a synthetic preparation of the endogenous Ah receptor ligand.

It is an object of the present invention to provide a preparation of analogs of the Ah receptor ligand.

It is an advantage of the present invention that the ligand preparation has the biochemical and physical properties described above.

Other advantages, features and objects will be apparent to one of skill in the art after examination of the specification, claims, and drawings.

BRIEF DESCRIPTION OF THE SEVERAL VIEWS OF THE DRAWINGS

FIG. 1 is a set of graphs describing cell response to βNF and tissue extracts. AhR ligand extraction and assays were conducted as described in the Examples. Error bars represent the standard deviations among observations from three assay wells. Each plot is a representative of similar experiments conducted numerous times. FIG. 1A. βNF dose response curve. Ordinate, luciferase activities expressed as relative light units (RLU). Abscissa, βNF concentration in ng/200 ul cell culture medium. FIG. 1B. Ligand activity in methanolic extracts from 1 gram of lung tissue of synthetic diet fed rats. Ordinate, βNF equivalents in ng. Abscissa: lung, the extracts from lung; Blank, the extracts from blank extraction, same as lung extraction but without lung tissue; DMSO, same quantity of DMSO used to deliver AhR ligands. FIG. 1C. Preliminary organ survey for Ah receptor ligand activities. Ordinate, BEQ (βNF equivalents in ng) in 1 gram of tissue. Abscissa, organs surveyed. FIG. 1D. Effect of base treatment on ligand activities from methanolic tissue extracts. Chloroform phases of the treatments are shown. The treatment labeled as base was treated with base as outlined in the Examples. The one indicated as N. Base (neutralized base) was treated the same as those treated with base except the base was neutralized first before adding the rest or the reagents. Blank is the blank extracts obtained the same time as tissue extract. Extract is the methanolic tissue extracts. Ordinate, βNF equivalents in ng; Abscissa: treatments. FIG. 1E. Effect of heat treatment alone on ligand activity from methanolic extracts. Ordinate, βNF equivalents in ng from 1 gram of lung tissue of synthetic diet fed rats. Abscissa, treatments. FIG. 1F. Effects of acid and heat treatments on ligand activities from methanolic extracts. Ordinate, βNF equivalents in ng from 1 gram of lung tissue of synthetic fed rats. Abscissa: treatments.

FIG. 2 is a set of graphs disclosing preliminary purification of AhR ligands.

FIG. 2A. Silica batch purification of acid and heat treated extracts from 5,000 grams of tissue. The procedure is outlined in the Examples. Aliquots from each fraction were assayed and the total activities from each fraction were calculated. Ordinate, βNF equivalents in μg from each fraction. Abscissa, fractions of batch purification. FIG. 2B. Silica gravity column chromatography of AhR ligands (120 μg BEQ). Solid line: ligand activities from different fractions. Dashed line, convex gradient of methanol in chloroform. Ordinate, βNF equivalents in μg. Abscissa, fraction numbers (125 ml each from fraction #1 to #7, 25 ml each from #8 to #88, 125 ml each from #89 to #106). Second ordinate, percentage of methanol in chloroform.

FIG. 3 is a set of graphs describing HPLC purification of AhR ligands. HPLC purification procedures were as described in the Examples. FIG. 3A. Purification of 50 μg BEQ of AhR ligand with a preparative silica HPLC column and methanol:chloroform mobile system. Solid line, ligand activities from different fractions. Dashed line, linear gradient of methanol in chloroform. Ordinate, ligand activity in BEQ (βNF equivalents in μg), Abscissa, fraction numbers (10 ml each from fraction #1 to #55, 20 ml each from #56 to #75, flow rate=10 ml/min). Second ordinate, percentage of methanol in chloroform. FIG. 3B. Purification of 40 μg BEQ of AhR ligands with a preparative silica HPLC column and isopropanol:hexane mobile system. Solid line, ligand activities from different fractions. Dashed line, linear gradient of isopropanol in hexane. Ordinate, ligand activity in BEQ (βNF equivalents in μg). Abscissa, fraction number (10 ml each from fraction #1 to #80, 20 ml each from #81 to #105, flow rate=10 ml/min.). Second ordinate, percentage of isopropanol in hexane. FIG. 3C. Purification of 20 μg BEQ of AhR ligand with a preparative C18 HPLC column and 75% methanol in water. Ordinate, ligand activities from different fractions in BEQ (μg). Abscissa, fraction numbers (5 ml each from fraction #1 to #30, 20 ml each from #31 to #55, flow rate: 5 ml/min. from 0 to 60 min, 10 ml/min. from 60 to 95 min). FIG. 3D. Purification of 10 μg BEQ of AhR ligand with an analytical C18 HPLC column and 50% acetonitrile in water. Ordinate, UV absorbance units at 356 nm. Abscissa, retention time in min. FIG. 3E. Purification of 10 μg BEQ of AhR ligand with a cyano HPLC column and 10% isopropoanol in hexane. Ordinate, UV absorbance units at 356 nm. Abscissa, retention time in min. FIG. 3F. Purification of 10 μg BEQ of AhR ligand with a cyano HPLC column and 60% methanol in water. Ordinate, UV absorbance units at 356 nm. Abscissa, retention time in minutes.

FIG. 4 is a set of graphs describing HPLC chromatogram and UV spectrum of the purified AhR ligand. FIG. 4A.

HPLC chromatogram of purified AhR ligand. The HPLC running condition was the same as described for UV spectroscopy in the Examples. X-axis, retention time in min. Y-axis, wavelengths monitored in nm. Z-axis, UV absorbance. FIG. 4B. UV spectrum of the AhR ligand. The procedure for data acquisition was outlined in the Examples. The spectrum was taken at an HPLC retention time of about 10 minutes at which moment the UV absorbance reached the maximum. X-axis, wavelengths in nm. Y-axis, UV absorbance.

FIG. 5 is a set of graphs describing electron impact mass and FT-IR spectra. FIG. 5A. High resolution electron impact mass spectrum of the AhR ligand. The data were taken and re-plotted as explained in the mass spectroscopy section of the Examples. X-axis, the ratio of mass to charge, m/z. Y-axis, relative abundance of ions. A sketched structure with the spectrum to show formation of the major fragments. Proposed fragmentation pathways are as mapped under the spectrum. FIG. 5B. FT-IR spectrum of Ah receptor ligand. The data were acquired as described in the Examples. X-axis, the frequencies of infrared beam expressed as wavenumber (cm$^{-1}$). The region from 1000 to 3000 cm$^{-1}$ is shown here. Y-axis, the absorbance. Signals with clear attribution are as labeled.

FIG. 6 is a graph and a table descrbing proton NMR spectrum and proton-carbon-13 correlation. FIG. 6A. $^1$H NMR spectrum of AhR ligand in d-methanol. Spectra were attained as described in NMR spectroscopy section of the Examples. The peak labeled with "Solvent" is contributed from NMR solvent. Signals contributed from numbers and locations of the protons are as labeled. FIG. B. Table of $^1$H—$^{13}$C correlation of the AhR ligand from both HSQC and HMBC spectra. The protons and carbon-13's with detectable connections are listed in the same row. The carbon-13's listed under a column headed "HSQC" are the ones directly connected (through one bond) to the corresponding proton(s) (in the same row) while the ones under the columns headed "HMBC" are connected to the corresponding proton(s) through two to three bonds.

FIG. 7 is a structure and graph describing the structure of ITE and dose responses of ITE and βNF. FIG. 7A. The structure of an endogenous Ah receptor ligand, 2-(1'H-indole-3'-carbonyl)-thiazole-4-carboxylic acid methyl ester. The chemical structure of the AhR ligand with its proton and carbon-13 chemical shifts (same as their identification numbers) are as labeled. FIG. 7B. Dose response curves of ITE and βNF after a 4 hour incubation. X-axis, concentrations of the agonists. Y-axis, reporter gene response to the agonists expressed as relative light units (RLU). The error bars represent the standard deviations among the observations from three culture wells.

DESCRIPTION OF THE INVENTION

In one embodiment, the present invention is a preparation of the endogenous Ah receptor ligand, analogs of the ligand, and therapeutic methods for using these preparations.

1. Biochemical Characterization of the AhR Ligand Preparation

The Examples below describe the preparation of the Ah receptor ligand from rat and pig lung. Preferably, the AhR ligand is of the formula displayed here and described at FIG. 7A.

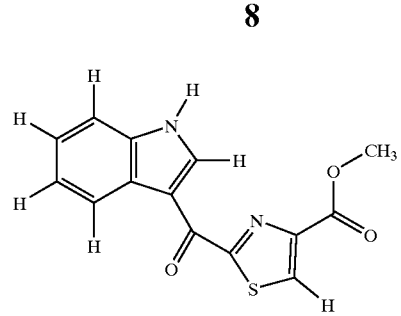

We envision that a successful preparation may be obtained from other animal organs, including liver, brain, bone, and muscle. The Examples below disclose that both the rat and pig lung preparations were successful. In a preferred preparation of the present invention, the preparation should be at least 60%, more preferably 90% and most preferably at least 95% pure based on HPLC analysis.

The Examples below disclose a preferred method for ligand extraction and purification. In brief, the animal organs are dissected and frozen on dry ice. The tissues are thawed and homogenized in PBS (buffered saline: 0.154 M NaCl, 10 mM phosphate buffer, pH 7.4) and extracted with methanol. This mixture is flushed with nitrogen gas, stirred, and centrifuged. The extract is heated at 100° C. with 2 N $H_2SO_4$, which renders the activity chloroform soluble. The activity is then purified through silica gel batch purification followed by large-scale gravity flow silica columns using methanol and chloroform gradients followed by high performance liquid chromatography on a preparative silica column and using a methanol/chloroform solvent elution. The activity is purified further on the HPLC silica columns using isopropanol/hexane gradients and then placed on a reverse-phase C18 HPLC column eluted with methanol and water. The material is further purified through a C18 column using acetonitrile/water and then through a cyano column using isopropanol/hexane. A final step includes HPLC using a cyano column and methanol/water elution.

The ligand activity is determined most preferably by an activity assay described below. In brief, the ligand extracts are added to Ah receptor-containing ligand reporter cells. These cells are then incubated for 4 hours and the cells are lysed to release the formed luciferase. This enzyme typically is measured according to the kit sold by Promega (Madison, Wis., USA.). Luciferase activity is measured by light emission recorded by a luminometer. The luminometer readings are taken after a substrate solution is injected into a well.

The preferred ligand preparation described below can be characterized by its solubility. The ligand is extractable from tissue by 80% methanol/20% water. After the boiling and acid treatment, the ligand is extractable in chloroform.

The ligand preparation is unstable in base but stable in up to two normal acid for at least 24 hours. The preparation is stable to heating at 37° C. overnight (16 hours) and at 100° C. for 24 hours.

The ligand preparation can be further characterized by its physical properties disclosed in the Examples, such as its ultraviolet, infrared, mass, and nuclear magnetic resonance spectra.

One of skill in the art will be able to prepare AhR ligand via the disclosed procedure or with modifications and optimizations apparent to one of skill.

We envision that one of skill in the art will wish to prepare analogs of the herein identified AhR ligand and screen these analogs for beneficial therapeutic usages. By "analog," we mean that the compound will have a structural similarity to the naturally occurring AhR ligand and will provide a beneficial therapeutic effect. The initial screen would be through the reporter gene assay described here. Further screenings would be devised according to the disease targeted.

Especially preferred are analogs corresponding to the formula:

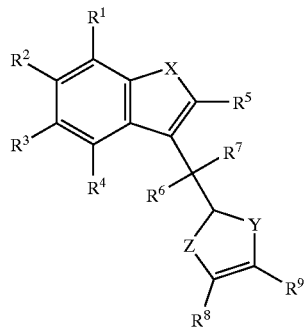

Where $R^1$, $R^2$, $R^3$, $R^4$, $R^5$, and $R^8$=H, lower alkyl (1–5 carbons), Br, F, Cl, O-acyl (1–5 C), or $OR^{10}$ where $R^{10}$=H, lower alkyl (1–5 C);

$R^6$ and $R^7$ taken together are =O; or when $R^6$=H, then $R^7$ can be H, OH, Br, F, Cl, $OR^{11}$ where $R^{11}$=alkyl (1–5 C);

when $R^7$=H, then $R^6$ can be H, OH, Br, F, Cl, $OR^{11}$ where $R^{11}$=alkyl (1–5 C);

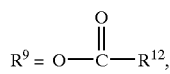

where $R^{12}$=H, alkyl (1–5 C), aryl, fluoro methyl, difluoro methyl, or trifluoro methyl; or $R^9$ can be

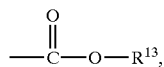

where $R^{13}$=H, alkyl (1–5 C), aryl, fluoro methyl, difluoro methyl, or trifluoro methyl; or $R^9$ can be

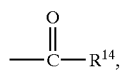

where $R^{14}$=H, alkyl (1–5 C), fluoro methyl, difluoro methyl, or trifluoro methyl; or $R^9$ can also be

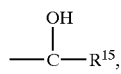

where $R^{15}$=alkyl (1–5 C), fluoro methyl, difluoro methyl, or trifluoro methyl, and X, Y, Z can be any of C, N, O, S.

Especially useful analogs are the following:

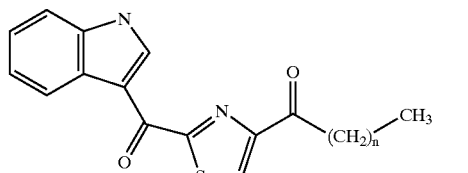

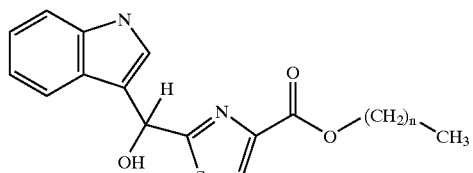

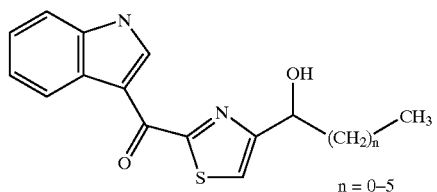

Additionally, one would wish to prepare therapeutic compounds comprising the above-identified ligand and ligand analogs. Preferably, one would provide pharmaceutically acceptable carriers for these compositions.

The ligand and its analogs can be administered orally and parenterally although the parenteral route is preferred for the AhR ligand itself. Presumably they can be provided in capsules, lozenges, tablets, or intravenously in suitable media. Suppositories or nasal delivery may also be used.

2. Use of the AhR Ligand

Identification of an endogenous AhR ligand in animal tissue and determination of its normal physiological function(s) will provide important new information on the mechanism of AhR-mediated biological responses. It is probable that such an endogenous ligand will be found to regulate cell growth and differentiation in a highly tissue-specific manner and to exhibit certain other responses that are caused by some of the known AhR ligands. Most importantly, we believe that the synthesis and testing of various structural analogs of the endogenous AhR ligand will lead to a new class of drugs for a wide variety of therapeutic applications.

Depending on the tissue and species, generalized responses to dioxin exposure consist of hyperplasia, hypoplasia, metaplasia, and dysplasia. These effects are believed to be mediated by alterations in homeostatic processes that are regulated by the interaction of growth factor signaling pathways, steroid hormone signaling pathways, and enzymes involved in the synthesis and degradation of these factors and hormones. There are a variety of different types of hormones involved in homeostasis at the cellular, tissue, organ, and organism level. Steroid hormones participate in the regulation of growth and development, sexual differentiation, reproduction, and cellular metabolism. Other hormones such as insulin regulate carbohydrate and fat metabolism. Decreases in estrogen receptor, glucocorticoid receptor, and insulin receptor concentrations have been reported following exposure to dioxin in laboratory animals. We envision that the endogenous AhR ligand and its analogs would alter the concentration of several hormones such as estrogen, progesterone, testosterone, vitamin A, and thyroid hormones and pituitary hormones such as luteinizing hormone in certain tissues.

There is a significant amount of evidence to indicate that humans are responsive to AhR agonists. Functional AhR's have been found in many human tissues including lymphocytes, liver, lung and placenta. Human CYP1A1 is inducible by dioxins in human lung and placenta. Decreased activity of the EGF receptor occurs in human placenta in women who were accidentally exposed to dioxin-like compounds and this same response has been reported in rodent tissues. Decreases in serum testosterone and increases in blood luteinizing hormone levels have been found in both humans and rats exposed to dioxins. There are reports of diabetes in workers exposed to dioxins as well as in Vietnam veterans exposed to dioxin present in the defoliant Agent Orange. Taken together, these findings indicate that dioxins, the human-made AhR ligands, can alter hormonal status in humans resulting in effects similar to those seen in laboratory animals Thus, humans are a responsive species to dioxin-like AhR agonists and are expected also to respond to the AhR ligand and its analogs disclosed here. Potential therapeutic uses of the present invention are given below.

Reduction of Body Weight. Dioxins decrease body weight resulting in a reduction in adipose tissue. While the exact mechanism for this effect is not known, there is evidence to suggest that it is due to a decrease in the "set point" for regulated body weight probably at the level of the hypothalamus. Dioxin is believed to decrease the "body weight set point" causing a dose-related decrease in food intake until the lower level of regulated body weight, determined by the dose of dioxin administered, is achieved. We envision the disclosed AhR ligand and its analogs have similar biological activity and would be useful, therapeutically, for body weight reduction in humans. In support of this possibility, humans accidentally exposed to dioxins report appetite suppression.

Immunosuppression or Immunostimulation. The immunotoxic effects of dioxins have been studied for several years, yet it is difficult to describe a dioxin-like immunotoxicity syndrome. In mice, dioxins suppress humoral and cell-mediated immunity. The resulting immunosuppression in mice leads to increased susceptibility to a variety of infectious agents. In rats, dioxin enhances the immune response to sheep red blood cells in the plaque forming cell assay while in the mouse, dioxin has the opposite effect and suppresses the response. In humans it is not known whether dioxin causes immunosuppression or immunostimulation, however, based on the animal studies, it is clear that dioxins and probably the AhR ligand disclosed here will modulate immune function. If the endogenous AhR ligand or its analogs cause immunosuppression, they will be useful in preventing transplant rejection and treatment of autoimmune diseases. On the other hand, if they cause immunostimulation, they could be used to treat immunodeficiency disorders such as acquired immunodeficiency syndrome (AIDS) and chronic infectious diseases.

Antiestrogen Action. Depending upon the context in which treatment occurs dioxin appears to inhibit the actions of estrogens in several laboratory animal species and in MCF cells in culture. In laboratory animals exposed to dioxin, fertility, litter size, and uterine weights are reduced. Furthermore, ovarian function is altered as indicated by anovulation and suppression of the estrous cycle. In rats and mice the antiestrogenic actions of dioxins occur at doses that do not alter body weight. The potential antiestrogenic activity of the endogenous AhR ligand and its analogs would be useful in the treatment of breast cancer and osteoporosis in humans.

Antiandrogen Action. In adult male rats, dioxin decreases testosterone production by inhibiting the rate-limiting step in testicular steroidogenesis. This results in a decrease in plasma concentrations of testosterone and dihydrotestosterone along with reductions in accessory sex organ weights. In male workers exposed to dioxins occupationally, it has been observed that there is a reduction in serum testosterone concentrations in association with increased plasma concentrations of follicle stimulating hormone and luteinizing hormone. The antiandrogen action of the disclosed AhR ligand and its analogs would be useful in the management of hyperplasia or cancer of the prostate, male pattern baldness, virilizing syndromes in women, precocious puberty in boys, and inhibition of sex drive in men who are sex offenders.

Treatment of Pulmonary Disorders. We envision that an AhR ligand preparation will be useful in treatment of pulmonary disorders such as (a) chronic obstructive pulmonary disease, (b) asthma, (c) emphysema, (d) bronchitis, (e) RQ mismatch, and (f) acute pulmonary dysfunction.

Control of Angiogenesis in Invasive Cancer. We envision that an AhR ligand preparation will be useful in the control of angiogenesis in invasive cancer. U.S. Pat. No. 6,323,228 describes compounds similar to the present invention, 3-substituted indole carbohydrazides, as useful for inhibiting angiogenesis. We envision that compounds of the present invention would be useful in treatment of both primary and metastasic solid tumors in carcinomas.

EXAMPLES

1. Ligand Extraction and Purification

Materials and Methods

Materials

All the solvents used were Burdick & Jackson grade (AlliedSignal Burdick & Jackson, Muskegon, Mich., USA) as long as available. The solvents were tested AhR ligand free before their use. Dimethyl Sulfoxide (DMSO, cat no. D-2650) used as vehicle for ligand dosing and β-Naphthoflavone (βNF, cat no. N-3633) used as AhR ligand for standard dose response curves were purchased from Sigma (St. Louis, Mo., USA). AhR ligand reporting cell line (H1L1.1C2, Garrison, et al., 1996) was kindly provided by Dr. Denison of University of California-Davis, Davis, Calif., USA Geneticin (G418, cat no. 11811-031), the antibiotics used in maintaining the ligand reporting construct in H1L1.1C2 cell line was purchased from GIBCO Life Technologies, Rockville, Md., USA.

Cell Culture

The cell line H1L1.1C2 was maintained in a culture medium (DMEM+10% FBS) with G418 at a concentration of 400 μg/ml and incubated under an atmosphere of 37° C., 6% $CO_2$, and 100% humidity. A 96 well sterile cell culture plate with about 30,000 cells per well in 200 μl of the culture medium without G418 was prepared and incubated for at least 12 hours before being dosed for ligand activity assay.

Ligand Activity Assay

The solvents from the ligand activities were evaporated and the activities were reconstituted in DMSO and 1 μl of this solution was used to dose the ligand reporting cells in a well with 200 μl of culture medium. One row of the reporting cells in each assay plate was dosed with 1 μl of the DMSO solutions of a set of βNF standards to generate a standard dose response curve. The dosed cells were incubated for 6 hours under the same environment as they were maintained. The cells were washed twice with a 1×PBS (pH 6.9) after the incubation and the culture wells were scanned under an inverted microscope to detect any obvious cell number change due to dosing. The cells were lysed by adding 50 μl of a 1×cell lysis reagent (Promega, Madison, Wis., USA) and 10 μl of the lysate from each well were transferred into a corresponding well of a Microlite 2 plate (Dynex Technologies Inc., Chantilly, Va., USA) for luminometer reading. A MLX Microtiter Plate Luminometer (Dynex Technologies Inc.) was programmed to inject 50 $\mu$l of a luciferase substrate solution (Promega) into a well, read the light intensities in Relative Light Units (RLU's) generated by the luciferase reaction for 5 seconds after a one second delay following the injection, and take the average of the 5 second readings as a final RLU.

Data Processing and Reporting

Dose response curves of RLU's vs. doses of $\beta$NF standards (ng in each assay well) from each plate were plotted and the RLU's generated by the samples were converted into $\beta$NF equivalent (BEQ) as ligand activity by consulting the $\beta$NF dose response curve generated from the same plate. Data were reported as ligand activity (in BEQ) vs. treatments or fractions from a purification procedure.

Tissue Collection and Homogenization

Tissues from a synthetic diet (diet 11, Suda et. al. 1970) fed Sprague Dawley rats were surgically removed from the euthanized animals, placed in clean polypropylene tubes, frozen on dry ice, and stored at $-80°$ C. until use. Porcine lung tissues removed from adult pigs (from market, 6 months old on average) freshly slaughtered at a slaughterhouse of Meat Science and Muscle Biology Laboratories at University of Wisconsin-Madison were collected, wrapped with new aluminum foil, frozen immediately on dry ice, and stored at $-80°$ C. until use. Tissues were cut when they were still cold and the cut tissues were transferred into a cleaned ice-cold glass bottle. The cut tissues to be homogenized were weighed to estimate the tissue volume (assuming 1 g tissue takes 1 ml in volume) and transferred into a cleaned glass cylinder for homogenization. One tissue volume of an ice-cold 1×PBS (freshly diluted from a 10×PBS: NaCl, 80 g/L; KCl, 2 g/L; $KH_2PO_4$, 5.8 g/L; $Na_2HPO_4$. $7H_2O$, 15.5 g/L; pH 6.2) was added to the homogenization cylinder. Tissues were homogenized with a PowerGene 700 homogenizer (Fisher Scientific, Pittsburgh, Pa., USA) and the volume of homogenate was measured. The parallel blank control was treated the same as for sample except there was no tissue, which was replaced by the same weight of 1×PBS. The smaller scale homogenization was conducted in a similar fashion except everything was scaled down.

Methanol Extraction

The homogenate was transferred into a cleaned 4 L solvent bottle. Four homogenate volumes of methanol were gradually added to the homogenate while stirring. The extraction mixture was flushed with argon and the extraction bottles were sealed with Teflon lined caps. The extraction mixture was stirred overnight in room temperature and transferred into a cleaned 1 L graded polypropylene centrifuge bottle. The extraction mixture was centrifuged at 1,000×g for 3 minutes in room temperature to separate the supernatant from the residues. Two residue volumes of a mixture of methanol:0.5×PBS (80:20, v/v) were added to the residues in centrifuge bottles. The centrifuge bottles were shaken to re-extract the tissue residues for 1 hour in room temperature. The mixture was centrifuged at 1,000×g for 3 minutes at room temperature and the pellets were discarded. The supernatants of the first and second extractions were pooled and the solvents were evaporated with a 12 L vacuumed flask in a water bath of 40° C. The extracts were quantitatively transferred with methanol to a cleaned 150 ml glass centrifuge bottle. The extracts were centrifuged at 4,000×g for 3 minutes in room temperature. The supernatants were transferred into another cleaned glass centrifuge bottle. About 20 ml of methanol for every 500 g of tissue equivalent were added to the pellet to re-extract the residues. The mixture was centrifuged again and the pellet was discarded. The supernatants were pooled and re-centrifuged at 4,000×g for 3 minutes in room temperature to pellet and discard the particles insoluble in methanol. The volume of extracts was reduced by evaporation to make a final solution of 10 g fresh tissue equivalent per milliliter of methanol. The extracts in methanol (10 g tissue/ml) were flushed with argon and stored in room temperature until further manipulations. The smaller scale extraction was conducted in a similar fashion with everything scaled down.

Base Treatment

An aliquot of methanolic extracts of about 4 ng BEQ was transferred into a cleaned glass vial and the solvents were evaporated. A solution (200 ul) of 0.1 N KOH in water was added into the vial. The vials were incubated at 37° C. overnight. After the incubation, the tubes were cooled down and neutralized slowly with HCl. The treatment mixtures were extracted with 200 $\mu$l of chloroform. Chloroform and aqueous phases were separated and the solvents were evaporated. DMSO (10 $\mu$l) was added to each tube for activity assay. $\beta$NF and blank extracts were treated the same way as for the sample. Initial results indicated that there was no activity in the aqueous phase from any treatment and therefore only chloroform phase was assayed for ligand activity in later experiments.

Heat Treatment

The methanolic extracts either in methanol or DMSO in a cleaned glass vials were heated in a 100° C. water bath for 30 minutes and the vials were cooled to room temperature. The extracts in the solvents were directly assayed as they were to determine the activities.

Acid and Heat Treatment

One volume of the extracts in methanol (10 g tissue/ml) was mixed with 1 volume of a 4 N $H_2SO_4$ in water. The treatment mixture was incubated at 37° C. overnight and then refluxed for 24 hours with stirring. The treatment mixture was cooled to room temperature and neutralized gradually to pH 6.5 to 6.9 with 10 N KOH. The treatment mixture was extracted three times with equal volumes of a water-saturated chloroform. The chloroform phases were pooled and the volume was reduced by evaporation to make a final solution of 30 g tissue equivalent per milliliter of chloroform. The treated extracts were flushed with argon and stored at 4° C.

Silica Gel Batch Purification

The silica gel (40 $\mu$m, Cat. no. 7024-02, J. T. Baker, Phillipsburg, N.J., USA) was cleaned sequentially with (2 silica gel volumes each time) methanol once, chloroform twice, hexane twice, chloroform once, and methanol twice. The cleaned silica gel was baked at 120° C. overnight before use. One and half liters of a 50% solution of chloroform in hexane were added to 500 g of silica gel. Extracts from 5,000 g of tissues in 160 ml chloroform were mixed with 160 ml hexane to bring the extracts into 50% chloroform in hexane and added to the silica gel in 50% chloroform in hexane while stirring. The silica gel was stirred for 30 minutes in room temperature and allowed to settle down. The solvents were removed and kept as "loading" fraction. Two liters of 50% chloroform in hexane were added to the silica gel. The silica gel was stirred for 5 minutes in room temperature before its settling down and the solvents were removed and kept as the "1st wash" fraction. The silica gel was washed with 2 L of chloroform as did for the first wash. The solvent was removed and kept as "2ed wash" fraction. Two liters of a 4% solution of methanol in chloroform were added to the silica gel to elute the activity. The silica gel was stirred for 5 minutes in room temperature and let to settle down. The solvents were removed and kept as the "1st elution" fraction. The elution step was repeated two time and the solvents were kept as "2ed elution" and "3rd elution" fractions, respectively. The silica gel was stripped with 2 L of methanol and the solvent was kept as the "1st stripping" fraction. A solution of 50% methanol in water was used to strip the silica gel second time and the fraction was labeled as the "2ed stripping" fraction. After the assay of aliquots from each fraction, the active fractions eluted with 4% methanol in chloroform were pooled and the solvents were evaporated. Chloroform was added to the pooled fractions to make a final solution of 10 ng βNF equivalent (BEQ) per microliter of chloroform. The batch purified extracts were flushed with argon and kept at 4° C.

Silica Gel Gravity Column Purification

A glass gravity column with ID of 8.1 cm was packed with 180 g of cleaned and freshly baked silica gel (same as that used for batch purification) in chloroform and let stand still for at least one hour. The column was equilibrated with 1 to 2 bed volumes of chloroform. About 400 µg BEQ of silica gel batch purified activity in chloroform were loaded onto the gravity column. Three bed volumes (~900 ml) of chloroform were run through the column. A convex gradient of 0 to 4% methanol in chloroform over 8 bed volumes (2,400 ml) was applied to elute the activity. Six bed volumes (1,800 ml) of methanol were used to strip the column. The active fractions eluted around 2% methanol in chloroform were combined after the ligand activity assay. The solvents were evaporated and chloroform was added to the pooled fractions to make a final solution of 30 ng BEQ per microliter. The purified extracts were flushed with argon and stored at 4° C.

Preparative Silica Column HPLC with Methanol:Chloroform

A preparative silica HPLC column (Zorbax Pro 10 silica, ID=21.5 mm) was equilibrated with chloroform at a flow rate of 10 ml/min. The silica gel gravity column purified activity (50 µg BEQ) brought into chloroform was injected into the column. Three column volumes (150 ml) of chloroform were pumped through the column. A linear gradient of 0 to 4% methanol in chloroform over 8 column volumes (400 ml) was then applied to elute the activity. The mobile phase was gradually changed into 100% methanol and 8 column volumes (400 ml) of methanol were used to strip the column. The active fractions eluted around 2% methanol in chloroform were pooled after the activity assay. The purified activity was flushed with argon and stored at −20° C.

Preparative Silica Column HPLC with Isopropanol:Hexane

The activity purified by the preparative silica HPLC column (methanol:chloroform system) was brought into 2% isopropanol in hexane at a concentration of 10 ng BEQ/ul. The mixture was centrifuged at 12,000×g for 5 minutes at room temperature. Four milliliters of the supernatant were injected into a silica HPLC column (Zorbax silica column, ID=21.5 mm) equilibrated with 2% isopropanol in hexane at a flow rate of 10 ml/min. Three column volumes (150 ml) of 2% isopropanol in hexane were pumped through the column. A linear gradient of 2 to 15% isopropanol in hexane was applied over 13 column volumes (650 ml) to elute the activities. The mobile phase was changed into 100% methanol over two column volumes (100 ml) and 8 column volumes (400 ml) of methanol were used to strip the column. The active fractions eluted around 5% isopropanol in hexane were pooled as "5% peak ligand". The ones eluted around 10% isopropanol in hexane were pooled as "10% peak ligand". The activities were flushed with argon and stored at −20° C.

Preparative C18 Column HPLC with 75% Methanol in Water

The "10% peak ligand" purified by the preparative silica HPLC column (isopropanol:hexane system) was brought into 75% methanol in water at a concentration of 4 µg BEQ/ml and centrifuged at 16,000×g for 3 minutes at room temperature in a cleaned polypropylene centrifuge tube. The supernatant was centrifuged one more time under the same condition. Five milliliters of the supernatant were injected into a preparative C18 HPLC column (Zorbax, ID=21.5 mm) equilibrated with 75% methanol in water at a flow rate of 5 ml/min. The HPLC was run isocratically with 75% methanol in water for 30 minutes (150 ml) and the mobile phase was changed into 100% methanol in 20 minutes (100 ml). The column was stripped with 100% methanol for 80 minutes (400 ml). The active fractions (5 ml each) with retention time of around 26 minutes were pooled. The activity was flushed with argon and stored at −20° C. in the mobile phase.

Analytical C18 Column HPLC with 50% Acetonitrile in Water

The activity of about 10 µg BEQ purified by the preparative C 18 HPLC column (75% methanol in water) was dissolved in 250 µl of 50% acetonitrile in water and centrifuged at 16,000×g for 3 minutes at room temperature in a cleaned polypropylene centrifuge tube. The supernatant was injected into an analytical C 18 column (Zorbax, ID=4.6 mm) equilibrated with 50% acetonitrile in water at a flow rate of 1 ml/min. From this purification step on, a Waters 996 photodiode array (PDA) detector (Waters Corp., Milford, Ma., U.S.A.) was used to take UV absorption data to establish a correlation between the biological activity of the ligand and its UV spectrum. Everything came from the column was allowed to flow through a flow cell (path length: 10 mm, ID: 0.009 in) of the PDA detector. UV Wavelengths monitored were initially set from 200 to 800 nm. After the spectrum of the compound became clear, a spectrum from 200 to 450 nm was monitored for the 10% peak ligand. The UV absorbance of the mobile phase was automatically set to zero. UV spectra were acquired with a Millennium 3.2 software (Waters Corp.) at a rate of one spectrum per second. The HPLC was conducted isocratically with 50% acetonitrile in water for 20 minutes and the mobile phase was changed into 100% acetonitrile in 10 minutes. The column was stripped with 100% acetonitrile for 20 minutes (20 ml). The fractions (0.5 ml each) constituting a characteristic UV spectrum of four peak absorbance at 208, 271, 277, and 355 nm at a retention time of about 7 minutes were pooled after confirming the biological activity. The pooled fractions were flushed with argon and kept at −20° C. in the mobile phase.

Analytical Cyano Column HPLC with 10% Isopropanol in Hexane

The activity of about 10 µg BEQ purified by the analytical C18 HPLC column (50% acetonitrile in water) was dissolved in 250 µl of 10% isopropanol in hexane and injected into an analytical cyano HPLC column (ID=4.6 mm, Adsorbosphere CN-AQ 5U, Alltech Associates, Inc. Deerfield, Ill., USA) equilibrated with 10% isopropanol in hexane at a flow rate of 1 ml/min. The column was run isocratically with 10% isopropanol in hexane for 20 minutes and the mobile phase was changed gradually into 100% methanol. The column was stripped with 100% methanol for 20 minutes (20 ml). The fractions (0.5 ml each) with the characteristic UV spectrum of four peak absorbance at 208, 271, 277, and 355 nm and a retention time of about 12 minutes were pooled after checking the biological activity. The ligands were flushed with argon and kept at −20° C. in the mobile phase.

Analytical Cyano Column HPLC with 60% Methanol in Water

The activity of about 10 μg BEQ purified by the analytical cyano HPLC column (10% isopropanol in hexane) was brought into 250 μl of 60% methanol in water. The solution was injected into the same cyano column equilibrated with 60% methanol in water at a flow rate of 0.5 ml/min. The column was run isocratically with 60% methanol in water for 20 minutes and the mobile phase was changed into 100% methanol in 10 minutes. The column was stripped with 100% methanol for 40 minutes (20 ml). The purified ligands were carefully collected following the UV absorbance. The UV spectrum of the purified ligands should be composed of four absorbing peaks at 208, 271, 277, and 355 nm, respectively, and the retention time should be around 10 minutes with this purification system. The ligands were flushed with argon and store in the mobile phase at −20° C.

Results

AhR Ligand Assay System and Extraction Procedure

We adapted a sensitive AhR ligand assay system (Garrison, et al., 1996) to a 96 well plate format to intensify, speed up, and semi-automate the assay. In the adapted assay system, 0.05 ng of βNF could be detected with confidence, which generated about two to three fold of induction over vehicle control. A distinguishable signal was generated with 0.01 ng of βNF and the maximum induction of this system is about 80 to 100-fold over vehicle (FIG. 1A). With the sensitive assay, we started the development of a reliable AhR ligand extraction procedure. We believed that an excellent source tissue for the ligand extraction might be lung tissue because human AhR gene was found to be transcribed abundantly in lung compared with other organs except placenta (Dolwick, et al., 1993). To decrease the possibility of environmental contamination, lung tissues from Sprague Dawley rats fed a synthetic diet (diet 11, Suda, et al., 1970) were used for test extractions. After rounds of tests, the extraction procedures were established as outlined in the method section. About 50 ng BEQ of ligand activity were detected in 1 gram of lung tissue extracted and there were no signals from either blank extraction or vehicle (FIG. 1B).

Source Tissue Determination for Ligand Extraction

With the established extraction procedure, we did a preliminary organ survey to identify an AhR-ligand-rich organ. The lung tissue of rats was found to have highest ligand activity among others examined (FIG. 1C). Based on the survey results, original reasoning, and data showing TCDD partitioning preferentially into rat and mouse liver other than lung (Santostefano, et al., 1996), we determined that source tissue for ligand extraction should be lung. To increase the yield, larger organs were needed. We, therefore, tested the ligand activities from lung tissues of pig and cow. Both sources showed similar ligand activity as the one from synthetic diet fed rats (data not shown). We chose pig as our source animal simply because it is the animal regularly slaughtered on University of Wisconsin-Madison campus.

Base Treatment

Once the ligand activities from animal tissues were extracted, we wanted to know preliminarily the nature of the activities. Since most of the non-physiological AhR ligands existing in the environment are very stable and resistant to strong base or acid treatments, we reasoned that a simple procedure at this moment to distinguish the endogenous activity from those of environmental contaminants would be the treatment of the extracted ligand activities with base or acid. As displayed in FIG. 1D, about 60 to 80% of the activities were abolished upon base treatment (0.1 N KOH, 37° C., overnight) while βNF or blank extracts did not respond to the treatment. The same condition of treatment but shorter incubation period (2 hours) also destroyed the activity (data not shown). The data suggested that the activity we extracted from animal tissues is not stable to base indicating that we were not isolating an environmental contaminant.

Heat Treatment

We tested whether heat treatment (100° C. water bath, 30 minutes) would reduce or destroy the extracted ligand activity. Heat treatment, unexpectedly, increased the activity of methanolic extracts 3 to 4-fold while vehicle, blank extracts, and βNF did not respond (FIG. 1E). Actually, the ligand activity of the methanolic extracts started to increase after a brief incubation of 5 minutes (data not shown). We believed that the heat treatment might help release the ligands from their possible carriers and the yield of ligand could be increased by this treatment.

Sulfuric Acid and Heat Treatment

Similarly, we tested the sulfuric acid treatment of the methanolic extracts and found the treatment also enhanced the ligand activity (data not shown). Combination of both sulfuric acid and heat treatment further increased the activity (FIG. 1F).

Silica Gel Batch and Gravity Column Purification

We used silica gel in both batch and gravity column formats to purify the acid and heat treated ligand. The ligand bound to silica gel could be washed with 50% chloroform in hexane and 100% chloroform without loss of activity. Most of the activity was eluted with 4% methanol in chloroform at the first round and two rounds of elution were sufficient to recover a large fraction of the activity (FIG. 2A). The activities extracted from 5,000 g of tissue could be efficiently purified with 500 g of freshly baked silica gel. The eluted activity dissolved in chloroform was then loaded onto a glass gravity column packed with the same silica gel and equilibrated with chloroform. A single peak of ligand activity co-migrated with a pink to brown band of materials and was eluted with 2% methanol in chloroform (FIG. 2B). The activity of about 400 μg BEQ could be purified with 180 g packed silica gel. The recovery of this system is around 25%.

HPLC Purification with Preparative Silica Columns

We injected the gravity column purified activity into a preparative silica HPLC column with methanol:chloroform mobile system. A single peak activity was eluted with 2% methanol in chloroform (FIG. 3A). The recovery from this system was about 90%. About 50 μg of BEQ could be purified with one injection into this system. The activities purified by this system were further purified by injecting the ligands into another preparative silica HPLC column with isopropanol:hexane solvent system. Two significant peaks of activity were eluted, respectively, with 5 and 10% of isopropanol in hexane in addition to some smaller peaks (FIG. 3B). We termed the active peak eluted with 5% isopropanol in hexane as the 5% peak ligand and, similarly, the one with 10% isopropanol in hexane as the 10% peak ligand. We pursued the 10% peak ligand. The purification capacity of this system is 40 μg of BEQ each injection and the recovery is around 20% for the total of two active peaks.

HPLC Purification with C18 Columns

We injected the 10% peak ligand into a preparative C18 HPLC column with a mobile phase of 75% methanol in water. A single peak of activity with a retention time of about 23 minutes (around fraction #23, 5 ml each fraction) was eluted (FIG. 3C). The recovery of the activities is about 80%. The activity purified by this system was injected into an analytical C18 HPLC column with a mobile phase of 50% acetonitrile in water. A UV absorption peak at 356 nm was eluted at a retention time of around 7 minutes (FIG. 3D), which coincided with ligand activity. The PDA data revealed a spectrum composed of 4 absorption peaks at 208, 271, 277, and 356 nm. As indicated in the chromatogram (FIG. 3D), the major 356 nm UV peak most of the time is accompanied with some UV absorbing contaminants. It was necessary to inject the activity into another HPLC system to remove those impurities. The recovery of this system is around 75% and the purification capacity is at least 15 $\mu$g BEQ for each injection.

HPLC Purification with an Analytical Cyano Column

We further purified the 10% peak ligands by injecting them into an analytical cyano HPLC column with a mobile system of 10% isopropanol in hexane. A UV absorption peak at 356 nm was eluted at a retention time of 12 minutes (FIG. 3E) that coincided with biological activity. The spectrum at that retention time was exactly the same as that appeared in previous step of purification (analytical C 18 HPLC column with 50% acetonitrile in water), indicating that the UV spectrum was the signature of the 10% peak ligand. The recovery of this system is about 80% and purification capacity at least 10 $\mu$g BEQ. It is necessary sometime to include another step of HPLC purification as indicated in FIG. 3E to eliminate completely the other UV absorbing contaminants. We used the same cyano column with a mobile phase of 60% methanol in water. A UV absorption peak at 356 nm was eluted at a retention time of 10 minutes (FIG. 3F). The recovery of this system is around 80% and the purification capacity at least 10 $\mu$g BEQ. The spectrum at the retention time is again the same as previous two steps of HPLC purification. The biological activity of the ligand, as expected, followed the UV spectrum confirming again it is the spectrum of the 10% peak ligand. The three dimensional chromatogram (FIG. 4A) shows that the ligand is away from any UV absorbing material at every wavelength (from 200 to 800 nm, not shown after 450 nm) monitored. The 10% peak ligand for the Ah receptor, therefore, is purified to homogeneity.

Overall Recovery and Yield of the 10% Peak Ligand

The overall recovery of the entire purification system is around 0.2% starting from batch purification to the last HPLC system. About 0.3 $\mu$g (absolute quantity) of the 10% peak ligand could be purified from an adult pig with about 500 grams of fresh lung tissue. We sequentially processed lung tissues from about 70 adult pigs and obtained approximately 20 $\mu$g of purified 10% peak ligand.

2. Structural Identification of the Ligand

Materials and Methods

UV Spectroscopy

A sample of about 3 $\mu$g $\beta$NF equivalents (BEQ) in 200 $\mu$l of methanol:water (60:40) was injected into a cyano HPLC column (adsorbosphere CN-AQ 5U, ID=4.6 mm, Alltech Associates, Inc. Deerfield, Ill., USA) equilibrated with 60% methanol in water at a flow rate of 0.5 ml/min. Compounds eluted from the column were allowed to flow through the flow cell (path length: 10 mm, ID:0.009 in) of a Waters 996 photodiode array detector (Waters Corp., Milford, Mass., USA). The UV absorbance of the mobile phase was automatically set to zero. UV spectra were recorded with a Millennium 3.2 software (Waters Corp.) at a rate of one spectrum per second as shown in FIG. 4A.

Electron Impact Mass Spectroscopy

A new glass probe was inserted into a MS50TC Ultrahigh Resolution Mass Spectrometer (Kratos Inc., Manchester, UK) with electron energy of 70 eV and ion source temperature of 150° C. The background spectrum for the probe was taken first. A blank spectrum for the injected solvent was determined on fractions that would have contained the ligand. A Kratos DS-55 data acquisition system was used to record all the spectroscopic data. The high-resolution spectroscopic data were re-plotted or tabulated after the subtraction of blank peaks.

FT-IR Spectroscopy

A sample of about 1 $\mu$g BEQ in methanol was spotted onto a Teflon STI IR Card (Thermo Spectra-Tech, Shelton, Conn., USA). The sample was applied to the card in such a way so that the area through which the smallest diameter infrared beam will pass was kept minimum to maximize the sample path length with limited supply of material. The solvent was evaporated and the card was placed in the sample chamber of an Infinity 60 AR FT-IR Spectrometer (Thermo-Mattson, Madison, Wis., USA). The spectrum was acquired with a WinFIRST 3.00 software (resolution: 2, scan number: 200, Iris opening: 1:, window: KBr). A blank spectrum was generated by solvent injection into the last purification step.

One-dimensional NMR Spectroscopy

A sample of about 2 $\mu$g in specified solvent placed in either a 2.5 mm NMR sample tube (Wilmad-Labglass, Buena, N.J., USA) or a 5 mm Shigemi tubes (Shigemi, Inc. Allison Park, Pa., USA) that have the magnetic susceptibility adjusted to that of the solvent was used to acquire the standard $^1$H NMR, single frequency decoupling, and single frequency NOE difference spectra. NMR spectra were obtained on Bruker DMX-750 and DMX-500 spectrometers (Bruker BioSpin Corp., Billerica, Mass., USA) located at the National Magnetic Resonance Facility at Madison. The spectrum of a blank (same fractions collected from a solvent injection of the last HPLC purification) was also recorded.

Two-dimensional NMR Spectroscopy

A sample of about 12 $\mu$g in deuterated methanol was placed in the 5 mm Shigemi tube (Shigemi, Inc.). The two-dimensional $^1$H{$^{13}$C} heteronuclear single quantum correlation (HSQC) (Schleucher, et al., 1994) and heteronuclear multiple bond correlation (HMBC) (Willker, et al., 1993) experiments were performed on the DMX-500 equipped with 5 mm triple-resonance, single-axis gradient Cryoprobe™ (Bruker BioSpin Corp.), which gives twice the signal-to-noise ratio of the DMX-750 spectrometer. Slight modifications were made to the gs-HMBC experiment. The direct peaks were not suppressed and a refocusing 180° pulse was applied to both $^1$H and $^{13}$C resonances at the midpoint of the antiphase buildup period to refocus static field inhomogeneities.

Theoretical Calculations

Proposed structures were constructed using the Gauss-View program (Gaussian Inc.). These models were subjected to full, unconstrained geometry optimization at the B3LYP/6-31 g* level of theory using the Jaguar quantum chemical program (Schrodinger Inc.). The absence of imaginary frequencies assured that the models were in a local ground state. Calculated frequencies were scaled using the SQM method on the optimized structures (Baker, et al., 1998). Isotropic chemical shifts were calculated from optimized models using the Gaussian suite of quantum chemical programs (Frisch, et al., 1998). The GIAO method at the B3LYP/6-311++G (2d,2p) level of theory as implemented in Gaussian 98 was used for the calculations. Calculated chemical shifts were calibrated versus experimental chemical shifts of some model compounds and the theoretical values were scaled empirically (Baldridge and Siegel. 1999; Rablen, et al., 1999; Forsyth and Sebag, 1997) using the following linear equations: Experimental shift ($^1$H, ppm)= Calculated shift *0.95+0.26; Experimental shift ($^{13}$C, ppm)=

Calculated shift #0.95+0.59. The $R^2$ values for the linear regressions were 0.999 for both $^1H$ and $^{13}C$ fits. Expected deviations of the calibrated theoretical chemical shifts from experimental values are ~0.15 ppm (Rablen, et al., 1999) for $^1H$ and ~3 ppm for $^{13}C$ (Baldridge and Siegel, 1999). The theoretical proton and carbon shifts of tetramethysilane (TMS) were set to zero.

Coupling constants were calculated by the single-finite-perturbation method (Onak, et al., 1999). The magnitude of the perturbation was 0.02 au, which is within the linear region of response, and the calculation was performed at the B3LYP/6-311+g* level of theory. In this method, only they Fermi contact contribution to the scalar coupling is available.

Reduction with $NaBH_4$

Specified quantity of the compound was pipetted into a glass via for reaction and the solvents were evaporated. A saturated solution (100 μl) of $NaBH_4$ in ethanol (200 proof, Aaper Alcohol and Chemical Co. Shelbyville, Ky., U.S.A.) was added to each reaction tube. The mixture was incubated overnight at room temperature and stopped by adding 200 μl of water. The reactions were extracted with 200 μl of chloroform twice and the chloroform phases were pooled. The solvents from both aqueous and chloroform phases were evaporated and both phases were assayed for biological activities. The chloroform phase was analyzed with electron impact mass spectroscopy as was a blank treated identically but containing no isolate.

Base Hydrolysis and Methylation

To 2 μl of methanol with 3 ng BEQ of the sample, 38 μl of methanol of 10 μl of a 0.5 mm KOH in water were added and mixed. The reaction was incubated at 37° C. for 2 hours and stopped by adding 10 μl of 0.5 mmolar HCl in water to bring pH to around 5.0. To the reaction mix, 30 μl of water, 10 μl of methanol, and 50 μl of chloroform were added and mixed. The chloroform phase was separated and kept after centrifugation of the mixture. The chloroform extraction was repeated and the two chloroform phases were pooled. The chloroform phase was split into two parts, one for biological assay and the other for methylation. The same manipulations were performed for 3 ng of βNF in 2 μl of methanol and 2 μl of methanol as controls.

For the methylation, the solvents were evaporated from the hydrolysis products and 50 μl of chloroform were added. The solution was cooled on ice and 5 μl of an ethereal solution of diazomethane (1 mg/1 ml, freshly prepared) was added. The reaction mixture was incubated on ice for 10 minutes with frequent shaking. The reaction was warmed to room temperature and centrifuged. The solvents were evaporated and the products were assayed side by side with the hydrolysis products without methylation.

Identities of Protons and Carbons in Structure Analysis

For the convenience of identification of atoms in the compound, protons and carbons are named after their chemical shifts. For example, a proton with a chemical shift of 9.25 ppm will be named as 9.25 proton and, similarly, a carbon of 141.05 ppm as 141 carbon.

Results

UV Spectroscopy

The UV spectrum of the sample shows a multiple peak absorption character. The first absorption peak appears at 208 nm and the next two are at 271 and 277 nm, which are smaller but distinctive. The last absorption peak appears at 356 nm (FIG. 4B). The spectrum is indicative of extensive conjugations. It is interesting that part of the spectrum (absorptions at 271 and 277 nm) resembles that of indole (Pretsch, et al., 2000).

Mass Spectroscopy

The high-resolution electron impact mass spectrum reveals that molecular ion of the sample is 286.0399 mass units and the molecular formula is $C_{14}H_{10}N_2O_3S$ (FIG. 5A, Table 1). The presence of sulfur is evidenced by the appearance of isotope cluster that shows the characteristic abundance of M+2 ion heavily contributed by $^{34}S$. The base peak is an ion with mass units of 144.0453 and constituted of $C_9H_6NO$. In addition to the molecular ion and the base peak, there are 116 ion that was derived from 144 ion by losing CO, 89 ion that was the product of losing CHN from the 116 ion, and 77 ion by losing $C_2HN$ from the 116 ion. There are some ions with relatively low abundance such as 271 ion derived from the molecular ion by losing $CH_3$, 258 ion formed by losing CO from the molecular ion, and the 227 ion generated by losing $CH_3$ and $CO_2$ from the molecular ion, indicative of methyl ester functionality. The other low abundance ions such as 200, 169,160,149,147, 142, 131, and 123 ions can be reasonably explained by the fragmentation processes involving one or two rearrangement events. Table 1 lists exact mass units of all the peaks with their molecular compositions, relative abundances, and deviations measuring the degrees of agreement between the experimental and theoretical mass.

TABLE 1

High-resolution EI Mass Fragments of the AhR Ligand

| Mass | Abundance (%) | Composition | Deviation |
| --- | --- | --- | --- |
| 288.0414 | 4.22 | $C_{14}H_{10}N_2O_3{}^{34}S$ | 14.93 |
| 287.0441 | 14.21 | $^{13}C_1{}^{12}C_{13}H_{10}N_2O_3S$ | 2.79 |
| 386.0399 | 69.19 | $C_{14}H_{10}N_2O_3S$ | 4.89 |
| 285.0361 | 4.64 | $C_{14}H_9N_2O_3S$ | 9.23 |
| 271.0172 | 3.49 | $C_{13}H_7N_2O_3S$ | 2.25 |
| 259.0437 | 0.62 | $^{13}C_1{}^{12}C_{12}H_{10}N_2O_2S$ | 24.32 |
| 258.0411 | 4.74 | $C_{13}H_{10}N_2O_2S$ | 20.54 |
| 228.0302 | 0.49 | $C_{12}H_8N_2OS$ | 24.73 |
| 227.0274 | 2.01 | $C_{12}H_7N_2OS$ | 2.69 |
| 226.0264 | 1.14 | $C_{12}H_6N_2OS$ | 27.52 |
| 200.0417 | 5.61 | $C_{11}H_8N_2S$ | 3.80 |
| 169.0394 | 1.96 | $C_{10}H_5N_2O$ | 5.03 |
| 160.0250 | 1.75 | $C_9H_6NS$ | 17.62 |
| 149.0263 | 2.50 | $C_8H_7NS$ | 24.89 |
| 148.0275 | 1.40 | $C_8H_6NS$ | 35.94 |
| 147.0688 | 1.2 | $C_9H_9NO$ | 2.24 |
| 145.0495 | 12.50 | $^{13}C_1{}^{12}C_8H_6NO$ | 9.80 |
| 144.0453 | 100.00 | $C_9H_6NO$ | 2.22 |
| 143.0383 | 2.89 | $C_9H_5NO$ | 8.04 |
| 142.0546 | 0.93 | $C_9H_6N_2$ | 10.00 |
| 131.0493 | 1.00 | $C_9H_7O$ | 3.13 |
| 123.0452 | 0.80 | $C_7H_7O$ | 4.80 |
| 117.0550 | 5.13 | $^{13}C_1{}^{12}C_7H_6N$ | 11.28 |
| 116.0503 | 28.98 | $C_8H_6N$ | 1.90 |
| 115.0435 | 2.02 | $C_8H_5N$ | 10.87 |
| 89.0393 | 12.00 | $C_7H_5$ | 1.68 |
| 88.0401 | 1.80 | $C_7H_4$ | 99.74 |
| 77.0401 | 1.50 | $C_6H_5$ | 12.33 |

FT-IR Spectroscopy

The FT-IR spectrum shows a strong absorption peak at 1737 $cm^{-1}$ the characteristics of a carbonyl, most probably an ester carbonyl (FIG. 5B). The presence of an ester is further supported by the existence of ester C—O peak around 1205 $cm^{-1}$. Peaks at 1435 and 2926 $cm^{-1}$ suggest the existence of a methyl and methoxy group. The peaks further support the existence of a methyl ester in agreement with the observation from high-resolution mass spectrum. A peak at 1593 $cm^{-1}$ is indicative of another carbonyl under a special structural environment in addition to the possible contribution from carbon-carbon double bonds, carbon-nitrogen double bonds, aromatic skeletons, and C=C in aromatic rings.

Proton NMR Spectroscopy

To reveal the 1d NMR signal contributed only from the purified compound with very low quantity, the spectra were taken from both sample and blank (same fractions as the sample from solvent injection of the last HPLC purification) in d-methanol and then both sample and blank in d-chloroform to avoid the possibility of overlapping between solvent and sample peaks. Chloroform made the spectrum complicated but served the purpose of revealing what was masked in the methanol spectrum. The 1d proton NMR spectrum of the sample reveals that there are 9 protons detected (FIG. 6A), the other one may be invisible due to exchange with the solvent used. The exchangeable proton (11.33 ppm) was visible when d-acetone was used as solvent (data not shown), confirming the molecular formula predicted from the high resolution mass spectroscopic data. The protons with chemical shifts of 7.27 (1 H), 7.28 (1 H), 7.50 (1 H), and 8.38 (1 H) are closely located on an aromatic ring with 7.27 and 7.28 protons in the middle supported further by the decoupling and NOE experiments (data not shown). There are three single peaks with chemical shifts of 9.25 (1 H), 8.67 (1 H), and 3.99 (3 H's) ppm. They are relatively isolated from each other and from the rest of the protons revealed by the decoupling and NOE experiments in d-methanol. When the NOE experiment was performed in d-acetone, however, both 7.50 and 9.25 protons responded when the 11.33 proton was irradiated, suggesting that those three protons are close spatially. The chemical shifts of 3.99 ppm and the 3.99 protons indicate that those protons are involved in a methoxy functionality supporting further the existence of methyl ester observed in both high resolution mass and FT-IR spectra. Judging from all the proton chemical shift values, all of them are most probably involved in aromatic systems except the 3.99 protons (FIG. 6A).

HSQC Spectroscopy

HSQC spectrum taken in d-methanol displays the chemical shifts of seven carbon-13's each with one or three protons attached (FIG. 6B). The 9.25 proton is attached to a carbon-13 with chemical shift of 141 ppm (141 carbon). Similarly, the 8.67, 8.36, 7.50, 7.28, 7,27, and 3.99 proton are attached, respectively, to the 135, 124, 114, 126, 125, and 55 carbons (FIG. 6B). Again, those carbon chemical shifts indicate that except for the 55 carbon they are involved in aromatic systems with some of them close to heteroatoms.

The 7.27 and 7.28 protons attached, respectively, to 125 and 126 carbons are separated on a spectrum when the resolution in both dimensions and acquisition time are increased. Their individual coupling patterns with neighboring protons are also revealed. Together with the 1d NMR spectrum, it is expected that both of them are more complicated than simple doublet doublet revealing that those two protons are located between the two other protons (7.50 and 8.36 protons).

HMBC Spectroscopy

The HMBC spectrum generated in d-methanol provides further detailed connectivity information (FIG. 6B). The 9.25 proton that is directly connected to 141 carbon is further linked, most probably through two to three bonds, to three other carbons with chemical shifts of 139,129, and 115 ppm. The 8.36 proton is directly connected to the 124 carbon and, at the same time, linked to the 126 carbon, which is directly connected to the 7.28 proton, and the 139 carbon which is also connected to the 9.25 proton through two to three bonds. Similarly, the 7.50 proton is directly connected to the 114 carbon and further connected to the 125 carbon, which in turn is directed connected to the 7.27 proton, and the 129 carbon which is also connected to the 9.25 proton more than one bond away. This relationship established that the 9.25 proton is four to five bonds away from both 7.5 and 8.36 protons. The 8.67 proton, on the other hand, is located on a relatively isolated system. It is connected to the carbons with chemical shifts of 150 and 173 ppm through two to three bonds in addition to the directly connected 135 carbon. None of the other protons shows any detectable connection to those three carbons. The 3.99 protons are shown to be connected to another carbon with chemical shift of 165 ppm (suggestive of ester carbonyl carbon) beside the directed connection to the 55 carbon (methyl carbon), in agreement with the methyl ester functionality. FIG. 6B shows detailed information on correlations between protons and carbon-13's. We have carbon chemical shift information on 13 out of total 14 carbons in the compound.

Some of the $^1H^{13}C$ coupling constants were directly measured from the HMBC spectrum. The coupling constant between the 9.25 proton and its directly connected carbon-13 (141 carbon) is 191 Hz and that of 8.67 proton and 135 carbon is 193 Hz. The two coupling constants reveal that both carbons are located close to a heteroatom in a 5 membered heteroaromatic ring. The one bond coupling constant between 7.27 (or 7.28) proton and 125 (or 126) carbon is 158 Hz confirming that those elements are involved in a 6 membered aromatic ring. The 3.99 protons have a coupling constant to their directly connected carbon (55 carbon) of 150 Hz confirming the methoxy functionality again.

Reduction

The reduction with NaBH4 completely destroyed the biological activity and changed dramatically the UV spectrum of the compound (data not shown). High-resolution mass spectrum was obtained after the reaction without purification. Even though the spectrum was complicated and might represent a mixture of reduction products, it is clear that the methoxy group was lost after the reduction because the molecular ion became 260 mass units and the molecular formula $C_{13}H_{12}N_2O_2S$. Again, this is indicative of existence of a methyl ester functionality.

Base Hydrolysis and Methylation

To confirm the existence of an ester, we first hydrolyzed the compound with KOH and checked the biological activity of the product. The biological activity of the hydrolysis product was completely lost (data not shown). When we methylated the hydrolysis product with diazomethane, about 60% of the ligand activity was recovered (data not shown) confirming the deduction of an ester functionality. When the same manipulations were carried out on βNF, no change in biological activity was detected. Further, blanks confirmed that none of the manipulations created biological activity.

The Structure

The high-resolution mass spectrum showing a molecular ion of 286.0399 ($C_{14}H_{10}N_2O_3S$) illustrates a highly condensed structure with only 10 protons. Further, a high degree of conjugation is revealed by the UV absorption spectrum (FIG. 4B). Four of these protons (7.27, 7,28, 7.50, and 8.36 protons) must be attached to a six membered aromatic ring. This ring is in turn fused with a five membered aromatic ring on which the 9.25 proton is attached. The 5 membered ring must be a heterocycle with either a nitrogen or an oxygen since the 144 base peak mass spectrum is composed of $C_9H_6NO$. However, oxygen cannot be a component of the five membered ring because the chemical shifts of two carbons directly connected to the oxygen would require a higher value than the HSQC and HMBC data would allow (FIG. 6B). A nitrogen, therefore, must be the component in the five membered ring resulting in an indole structure. To satisfy the composition of $C_9H_6NO$ for the 144 base mass peak, one of the positions on the five membered ring must be substituted with either a C=O or C—O moiety. Considering the fact that both 9.25 and 8.36 protons are highly deshielded, there must be groups located between the 9.5 and 8.36 protons. Thus, the 9.25 proton must be located between the nitrogen and the substituted carbon, further confirming the indole structure.

The above mentioned C—O or C=O moiety could be a C—O in a six membered ring, which will not deshield its neighboring protons, or an attached ketone with deshielding power. That a ketone on a carbon attached to the indole nucleus exists is supported by the infrared band at 1593 cm$^{-1}$ (FIG. 5B), characteristic ketones on a carbon in the vicinity of an indole as revealed by model compounds such as 3-benzoylindole (SDBS Data base, Bergman and Venemalm, 1990), (cyclohex-1-en-1-yl)-3-indolylmethanone, and 3-(E-2-methylbut-2-enoyl) indole (Bergman and Venemalm, 1990). This ketone is attached to another five membered heteroaromatic ring (either thiazole or isothiazole).

Considering both proton and carbon chemical shifts of thiazole and isothiazole and the fact that the two other positions will be substituted by two groups with deshielding power, only the 5-position can be considered for the 8.67 proton attachment in the case of thiazole structure. With the 2- and 4-positions attached to ketone and the methyl ester, respectively, or vice versa, there will be two possible structures based on thiazole. Similar to the thiazole situation, there are two possible structures based on isothiazole because only the 4-position can be considered for the 8.67 proton attachment.

The $^1H$—$^{13}C$ coupling constant for the 8.67 proton to its directly attached carbon derived from the HMBC spectrum is about 193 Hz. We investigated the coupling constants between the position 5 proton and carbon in thiazole and the position 4 proton and carbon in isothiazole. Faure, et al., (1978) and Tseng (1987) reported that the coupling constant between the position 5 proton and carbon in thiazole is about 191 Hz and the range is from 188 to 200 with different substitutions at the other positions while the one between the position 4 proton and carbon in isothiazole is about 173 Hz only and the range is from 168 to 171 with different substitutions at the other positions. Furthermore, we calculated the theoretical coupling constants for both thiazole and isothiazole based structures. The theoretical coupling constant between the 8.67 proton and its connected carbon in thiazole structure is 185.4 Hz while that in isothiazole based structure is 175.7 Hz.

Judging from both theoretical coupling constants and the experimental values in literature, the isothiazole structures were eliminated. Of the thiazole structures, one is derived from cysteine in which the position 2 of thiazole is substituted with a ketone and position 4 a methyl ester (FIG. 7A). The other is non-cysteine related with reversed order of substitution as shown in FIG. 7A.

The chemical shift theoretical calculation results show that the cysteine related structure best fits the experimental values. Evidence from experimental data in literature supports this deduction. When an aldehyde (equivalent to a ketone in this case) connected to the 2 position of the thiazole, the chemical shift of carbon 2 is 166 ppm and carbon 4 is 146 ppm (Dondoni and Perrone, 1995). When a methyl ester is attached to the 4 position of the thiazole, the chemical shift of carbon 4 is 146 ppm and the carbon 2 (with a methyl group attached) is 167 ppm (Mensching and Kalesse, 1997). We can confidently deduct that when an aldehyde (or a ketone) is attached to carbon 2 and a methyl ester to carbon 4 of a thiazole at the same time, similar to the arrangement of the cysteine related structure, the chemical shift of carbon 2 and 4 will be 166 and 146, respectively, which agrees with both calculated and measured chemical shifts for this structure (FIG. 7A). On the other hand, when an aldehyde (or a ketone) is connected to the 4 position of a thiazole, the chemical shift of carbon 4 is 155 (Nicolaou, et al., 1997) or 156 (Millan, et al., 2000). If a methyl ester substitutes the 2 position of a thiazole, the chemical shift of carbon 2 is 158 ppm (Kelly and Lang, 1995). Thus, if an aldehyde (or a ketone) is attached to the 4 position and a methyl ester to the 2 position at the same time, similar to the arrangement of the non-cysteine related structure, the chemical shifts of carbon 4 and 2 will be, respectively, 155 and 158 ppm, which agrees well with what is calculated for this structure (158 and 163 ppm). Thus, the experimental data and the calculated chemical shifts leave no doubt that the correct structure is the cysteine related as shown in FIG. 7A, which represents an endogenous Ah receptor ligand.

Additional support for the ligand structure of FIG. 7A is provided by the electron impact mass spectrum of 3-benzoylindole (SDBS Database, Bergman and Venemalm, 1990). The molecular ion for the compound is 221 mass units. As soon as an ion composed of indole connected to a ketone formed after losing the benzene, the base peak of 144 appears because of its high stability. Further fragmentation pattern of this known compound is exactly the same as that of our purified ligand: loss of CO from the 144 peak gives the 116 peak and loss of CHN (or $C_2HN$) from the 116 peak yields the 89 (or 77) peak (SDBS Database).

Thus, the novel Ah receptor ligand is deduced as 2-(1'-H-indole-3'-carbonyl)-thiazole-4-carboxylic acid methyl ester, which we shorthandedly refer to as ITE. To be sure of the structure, chemical synthesis was initiated and the synthetic compound produced provided the same biological activity and the same physical data as that obtained with the isolate. The reporter gene activity as a function of doses of ITE as compared to that of βNF is shown in FIG. 7B, indicating about five times as potent as that of βNF after 4 hours of incubation, which is the optimum time point from a time course experiment (data not shown). The action of ITE through the Ah receptor was demonstrated by the ability of an AhR antagonist, 3'-methoxy-4'-nitroflavone (Henry, et al., 1999), to block the reporter gene response to the compound in a dose dependent fashion (data not shown).

References

Adachi, J. et al. "Indirubin and indigo are potent aryl hydrocarbon receptor ligand present in human urine". *J. Biol. Chem.* 276(34):31475–31478 (2001).

Alexander, D. L., Ganem, L. G., Fernandez-Salguero, P., Gonzalez, F., and Jefcoate, C. R. "Aryl-hydrocarbon receptor is an inhibitory regulator of lipid synthesis and of commitment to adipogenesis". *J. Cell Sci.* 111 (Part 22):3311–3322 (1998).

Baker, J., et al. "Direct Scaling of Primitive Valence Force Constants: An Alternative Approach to Scaled Quantum Mechanical Force Fields," *J. Phys. Chem. A* 102:1412–1424, 1998.

Baldridge, K. K. and J. S. Siegel, "Correlation of Empirical .delta.(TMS) and Absolute NMR Chemical Shifts Predicted by ab Initio Computations," *J. Phys. Chem. A* 103:4038–4042, 1999.

Benedict, J. C., Lin, T. M., Loeffler, I. K., Peterson, R. E., and Flaws, J. A. "Physiological role of the aryl hydrocarbon receptor in mouse ovary development". *Toxicol. Sci.* 56(2):382–388 (2000).

Bergman, J. and L. Venemalm, "Acylation of the Zinc Salt of Indole, *Tetrahedron* 46(17):6061–6066, 1990.

Bonnesen, C., Eggleston, I. M., and Hayes, J. D. "Dietary indoles and isothiocyanates that are generated from cruciferous vegetables can both stimulate apoptosis and confer protection against DNA damage in human colon cell lines". *Cancer Res.* 61(16):6120–6130 (2001).

Burbach, K. M., Poland, A. and Bradfield, C. A., "Cloning of the Ah-receptor cDNA reveals a distinctive ligand-activated transcription factor," *Proc. Natl. Acad. Sci. USA* 89:8185–8189 (1992).

Chen, I., Safe, S., and Bjeldanes, L. "indole-3-carbinol and diindolylmethane as aryl hydrocarbon (Ah) receptor agonists and antagonists in T47D human breast cancer cells". *Biochem. Pharmacol.* 51(8):1069–1076 (1996).

Chen, Y. H. et al. "Regulation of CYP1A1 by indolo[3,2-b]carbazole in murine hepatoma cells". *J. Biol. Chem.* 270(38):22548–22555 (1995).

Cheung, Y. L., Snelling, J., Mohammed, N. N. D., Gray, T. J. B., and Ioannides, C. "Interaction with the aromatic hydrocarbon receptor, cyp1a induction, and mutagenicity of a series of diaminotoluenes—implications for their carcinogenicity". *Toxicol. Appl. Pharmacol.* 139(1):203–211 (1996).

Dolwick, K. M., Schmidt J. V., Carver L. A., Swanson H. I., Bradfield C. A. "Cloning and expression of a human Ah receptor cDNA". *Mol. Pharmacol.* 44:911–917 (1993).

Dolwick, K. M., Swanson H. I., Bradfield C. A. "In vitro analysis of Ah receptor domains involved in ligand-activated DNA recognition". *Proc. Natl. Acad. Sci. U.S.A.* 90:8566–70 (1993).

Dondoni, A. and D. Perrone, "Total Synthesis of (+)-Galactostatin. An Illustration of the Utility of the Thiazole-aldehyde Synthesis," *J. Org. Chem.* 60:4749–4754 (1995).

Elferink, C. J., Ge, N. L., and Levine, A. "Maximal aryl hydrocarbon receptor activity depends on an interaction with the retinoblastoma protein". *Mol. Pharmacol.* 59(4):664–673 (2001).

Elizondo, G. et al. "Altered cell cycle control at the G(2)/M phases in aryl hydrocarbon receptor-null embryo fibroblast". *Mol. Pharmacol.* 57(5): 1056–1063 (2000).

Faure, R., Galy, J., Vincent, E., and Elguero, J. "Etudes d'heterocycles pentagonaux polyheteroatomiques par resonance magnetique nucleaire du $^{13}$C, Thiazoles et thiazolo[2,3-e]tetrazoles," *Can. J. Chem.* 56:46–55 (1978).

Fernandez-Salguerro, P. et al. "Immune system impairment and hepatic fibrosis in mice lacking the dioxin-binding Ah receptor," *Science* 268:722–726 (1995).

Fletcher, N., Hanberg, A., and Hakansson, H. "Hepatic vitamin A depletion is a sensitive marker of 2,3,7,8-tetrachlorodibenzo-p-dioxin (TCDD) exposure in four rodent species". *Toxicol. Sci.* 62(1):166–175.(2001)

Forsyth, D. A. and Sebag, A. "Computed 13C NMR Chemical Shifts via Empirically Scaled GIAO Shieldings and Molecular Mechanics Geometries. Conformation and Configuration from 13C Shifts," *J. Am. Chem. Soc.* 119:9483–9494 (1997).

Frisch, M. J., et al., "Gaussian 98, Revision A.9." Gaussian Inc., Pittsburgh, Pa., USA, (1998).

Garrison, P. M. et al. "Species-specific recombinant cell lines as bioassay systems for the detection of 2,3,7,8-tetrachlorodibenzo-p-dioxin-like chemicals," *Fund. Appl. Toxicol.* 30:194–203 (1996).

Gradin, K. et al. "Functional interference between hypoxia and dioxin signal transduction pathways: competition for recruitment of the Arnt transcription factor". *Mol. Cell. Biol.* 16(10):5221–31 (1996).

Gu, Y., Hogenesch, J. B., and Bradfield, C. A. "The PAS superfamily: sensors of environmental and developmental signals". *Ann. Rev. Pharmacol. Toxicol.* 40:519–561 (2001).

Heathpagliuso, S. et al. "Activation of the Ah receptor by tryptophan and tryptophan metabolites". *Biochem.* 37(33):11508–11515 (1998).

Hogenesch J. B., et al., "Characterization of a subset of the basic-helix-loop-helix-PAS super family that interacts with components of the dioxin signaling pathway," *J. Biol. Chem.* 272:8581–8593 (1997).

Jain S., Dolwick K. M., Schmidt J. V., Bradfield C. A., "Potent transactivation domains of the Ah receptor and the Ah receptor nuclear translocator map to their carboxyl termini," *J. Biol. Chem.* 269:31518–31524 (1994).

Jellinck, P. H. et al. "Ah receptor binding properties of indole carbinols and induction of hepatic estradiol hydroxylation". *Biochem. Pharmacol.* 45(5):1129–1136 (1993).

Kelly, T. R. and F. Lang, "Synthesis of Thiazole Compounds via Lithiation: An Unexpected Rearrangement," *Tetrahedron Letters* 36(51):9293–9296 (1995).

Kleman, M. I., Poellinger, L., and Gustafsson, J. A. "Regulation of human dioxin receptor function by indolocarbazoles, receptor ligands of dietary origin". *J. Biol. Chem.* 269(7):5137–5144 (1994).

Lee, I. J. et al. "Transcriptional induction of the cytochrome p4501a1 gene by a thiazolium compound, yh439". *Mol. Pharmacol.* 49(6):980–988 (1996).

Liu, R. M.et al. "Regulation of [Ah] gene battery enzymes and glutathione levels by 5,10-dihydroindeno[1,2-b] indole in mouse hepatoma cell lines". *Carcinogenesis.* 15(10):2347–2352. (1994).

Maltepe, E. and Simon, M. C. "Oxygen, genes, and development: an analysis of the role of hypoxic gene regulation during murine vascular development". *J. Mol. Med.* 76(6):391–401 (1998).

McDougal, A., Wormke, M., Calvin, J., and Safe, S. "Tamoxifen-induced antitumorigenic/antiestrogenic action synergized by a selective aryl hydrocarbon receptor modulator". *Cancer Res.* 61(10):3902–3907 (2001).

McDougal, A., Sethi-Gupta, M., Ramamoorthy, K., Sun, G., and Safe, S. "Inhibition of carcinogen-induced rat mammary tumor growth and other estrogen-dependent responses by symmetrical dihalo-substituted analogs of diindolylmethane". *Cancer Lett.* 151:169–179 (2000).

Mensching, S. and M. Kalesse, "Generation of Thiazoles by Column Dehydrogenation of Thiazolidines with $MnO_2$," *J. Prakt. Chem.* 339:96–97 (1997).

Millan, D. S., et al., "The Synthesis and Activity of Oxazole and Thiazole Analogues of Urocanic Acid," *Tetrahedron* 56:811–816, (2000).

Mimura, J. et al. "Loss of teratogenic response to 2,3,7,8-tetrachlorodibenzo-p-dioxin (TCDD) in mice lacking the Ah (dioxin) receptor". *Gene. Cell.* 2:645–654 (1997).

Nicolaou, K. C., et al., "Total Syntheses of Epothilones A and B via a Macrolactonization-based Strategy," *J. Am. Chem. Soc.* 119:7974–7991 (1997).

Okamoto, T., Mitsuhashi, M., Fujita, I., Sindhu, R. K., and Kikkawa, Y., "Induction of cytochrome P450 1A1 and 1A2 by hyperoxia," *Biochem. Biophys. Res. Commun.* 197:878–885 (1993).

Onak, T., et al., "Density Functional Theory/Finite Perturbation Theory Calculations of Nuclear Spin-Spin Coupling Constants for Polyhedral Carboranes and Boron Hydrides," *J. Am. Chem. Soc.* 121:2850–2856 (1999).

Phelan, D., Winter, G. M., Rogers, W. J., Lam, J. C., and Denison, M. S. "Activation of the Ah receptor signal transduction pathway by bilirubin and biliverdin". *Arc. Biochem. Biophy.* 357(1):155–163 (1998).

Poellinger, L. "Mechanistic aspects-the dioxin (aryl hydrocarbon) receptor". *Food Add. Contam.* 17(4):261–266 (2000).

Poland, A., Glover, E., and Kende, A. S. "Stereospecific, high affinity binding of 2,3,7,8-tetrachlorodibenzo-p-dioxin by hepatic cytosol: evidence that the binding species is receptor for induction of aryl hydrocarbon hydroxylase". *J. Biol. Chem.* 251:4936–4946 (1976).

Poland, A. and Glover, E. "Chlorinated dibenzo-p-dioxin: Potent inducers of □-aminolevulinic acid synthetase and aryl hydrocarbon hydroxylase. II. A study of the structure-activity relationship". *Mol. Pharmacol.* 9:736–747 (1973).

Preobrazhenskaya, M. N. and Korolev, A. M. "Indole derivatives in vegetables of the Cruciferae family". *Bioorganicheskaya Khimiya.* 26(2):97–111 (2000).

Pretsch, E., et al., "Structure Determination of Organic Compounds: Tables of Spectral Data," $3^{rd}$ ed., Springer, Berlin, N.Y., 2000.

Probst, M. R., Reisz-Porszasz, S., Agbunag, R. V., Ong, M. S. and Hankinson, O., "Role of the aryl hydrocarbon receptor nuclear translocator protein in aryl hydrocarbon (dioxin) receptor action," *Mol. Pharmacol.* 44:511–518 (1993).

Puga, A., et al. "Aromatic hydrocarbon receptor interaction with the retinoblastoma protein potentiates repression of E2F-dependent transcription and cell cycle arrest." *J. Biol. Chem.* 275(4):2943–2950 (2000).

Rablen, P. R., et al., "A Comparison of Density Functional Methods for the Estimation of Proton Chemical Shifts with Chemical Accuracy," *J. Phys. Chem. A* 103:7357–7363 (1999).

Rannug, U., Rannug, A., Sjoberg, U., Li, H., Westerholm, R., and Bergman, J. "Structure elucidation of two tryptophan-derived, high affinity Ah receptor ligands". *Chem. Biol.* 2(12):841–845 (1995).

Rannug, A. et al. "Certain photooxidized derivatives of tryptophan bind with very high affinity to the Ah receptor and are likely to be endogenous signal substances," *J. Biol. Chem.* 262:15422–15427 (1987).

Safe, S. "Molecular biology of the Ah receptor and its role in carcinogenesis". *Toxicol. Let.* 120:1–7 (2001).

Santostefano, M. J. et al. "Subcellular localization of TCDD differs between the liver, lungs, and kidneys after acute and subchroni exposure: species/dose comparisons and possible mechanism". *Fund. Appl. Toxicol.* 34:265–275 (1996).

Schaldach, C. M., Riby, J., and Bjeldanes, L. F. "Lipoxin A(4): A new class of ligand for the Ah receptor". *Biochem.* 38(23):7594–7600 (1999).

Schleucher, J., et al., "A General Enhancement Scheme in Heteronuclear Multidimensional NMR Employing Pulsed Field Gradients," *J. Biomol. NMR.* 4:301–306 (1994).

Schmidt, J. V. and Bradfield, C. A. "Ah receptor signaling pathways". *Ann. Rev. Cell Dev. Biol.* 12:55–89 (1996).

Schmidt, J. V., Su, G. H., Reddy, J. K., Simon, M. C., and Bradfield, C. A. "Characterization of a murine Ahr null allele: involvement of the Ah receptor in hepatic growth and development". *Proc. Nat. Acad. Sci. USA.* 93:6731–6736 (1996).

SDBS Database, Integrated Spectral Data Base System for Organic Compounds, National Institute of Advanced Industrial Science and Technology, Tsukuba, Ibaraki, Japan, SDBS Web: http://www/aist.go/ip/riodb/sdbs/

Shimba, S., Wada, T., and Tezuka, M. "Arylhydrocarbon receptor (AhR) is involved in negative regulation of adipose differentiation in 3T3-L1 cells: AhR inhibits adipose differentiation independently of dioxin". *J. Cell Sci.* 114(15):2809–2817 (2001).

Shimba, S., Todoroki, K., Aoyagi, T., and Tezuka. M. "Depletion of arylhydrocarbon receptor during adipose differentiation in 3T3-I1 cells". *Biochem. Biophy. Res. Corn.* 249(1):131–137 (1998).

Sinai, C. J. and Bend, J. R. "Aryl hydrocarbon receptor-dependent induction of cyp1a1 by bilirubin in mouse hepatoma hepa 1c1c7 cells". *Mol. Pharmacol.* 52(4):590–599 (1997).

Stephensen, P. U. et al. "N-methoxyindole-3-carbinol is a more efficient inducer of cytochrome P-450 1A1 in cultured cells than indol-3-carbinol". *Nutr Cancer Internatl. J.* 36(1):112–121 (2000).

Suda, T., DeLuca, H. F., and Tanaka, Y. "Biological activity of 25-hydroxyergocalciferol in rats". *J. Nutrition.* 100(9):1049–1052 (1970).

Swanson, H. I. and Bradfield, C. A., "The Ah-receptor: Genetics, structure and function," *Pharmacogenetics* 3:213–230 (1993).

Tian H., McKnight S. L., Russell D. W., "Endothelial PAS domain protein 1 (EPAS1), a transcription factor selectively expressed in endothelial cells," *Genes Dev.* 11:72–82 (1997).

Tseng, C. K., "Proton and Carbon-13 NMR Studies of 2-Aminothiozoles and 2-Iminothiazolines," *Magn. Reson. Chem.* 25:105–108 (1987).

Vasiliou, V., Shertzer, H. G., Liu, R. M., Sainsbury, M., and Nebert, D. W. "Response of [Ah] battery genes to compounds that protect against menadione toxicity". *Biochem. Pharmacol.* 50(11):1885–1891 (1995).

Washburn, B. S. et al. "Brevetoxin-6 (pbtx-6), a nonaromatic marine neurotoxin, is a ligand of the aryl hydrocarbon receptor". *Arc. Biochem. Biophy.* 343(2):149–156 (1997).

Whitlock, J. P. Jr. et al. "Induction of drug-metabolism enzymes by dioxin". *Drug Metabol. Rev.* 29:1107–1127 (1997).

Whitlock, J. P., Jr., "Genetic and molecular aspects of 2,3,7,8-tetrachlorodibenzo-p-dioxin action," *Ann. Rev. Pharmacol. Toxicol.* 30:251–277 (1990).

Wilk, R. Weizman, I. and Shilo, B.-Z., "Tracheless encodes a bHLH-PAS protein that is an inducer of tracheal cell fates in Drosophila," *Genes Dev.* 10:93–102 (1996).

Willker, W., et al., "Gradient Selection in Inverse Heteronuclear Correlation Spectroscopy," *Magn. Reson. Chem.* 31:287–292 (1993).

We claim:

1. An isolated preparation of endogenous Ah receptor ligand wherein the ligand has the following formula:

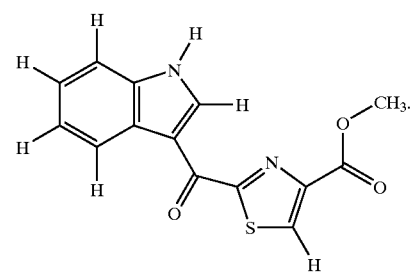

2. A therapeutic preparation of the endogenous Ah receptor ligand of claim 1.

3. The preparation of claim 2 wherein the preparation is at least 90% pure.

4. The preparation of claim 3 wherein the preparation is at least 95% pure.

5. The preparation of claim 2 wherein the ligand is isolated from animal tissues.

6. The preparation of claim 1 wherein the isolated preparation is at least 90% pure.

7. The preparation of claim 1 where the preparation is at least 95% pure.

* * * * *